(12) United States Patent
Luxenhofer et al.

(10) Patent No.: US 12,018,125 B2
(45) Date of Patent: Jun. 25, 2024

(54) BLOCK-COPOLYMERS FOR THE DELIVERY OF ACTIVE AGENTS

(71) Applicant: JULIUS-MAXIMILIANS-UNIVERSITÄT WÜRZBURG, Würzburg (DE)

(72) Inventors: Robert Luxenhofer, Würzburg (DE); Michael Lübtow, Würzburg (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 1021 days.

(21) Appl. No.: 16/623,513

(22) PCT Filed: Jun. 19, 2018

(86) PCT No.: PCT/EP2018/066301
§ 371 (c)(1),
(2) Date: Dec. 17, 2019

(87) PCT Pub. No.: WO2018/234329
PCT Pub. Date: Dec. 27, 2018

(65) Prior Publication Data
US 2021/0147627 A1    May 20, 2021

(30) Foreign Application Priority Data

Jun. 20, 2017   (EP) .................................... 17176886

(51) Int. Cl.
*C08G 73/02*   (2006.01)
*A61K 9/107*   (2006.01)
(Continued)

(52) U.S. Cl.
CPC ........ *C08G 73/0233* (2013.01); *A61K 9/1075* (2013.01); *C08F 291/12* (2013.01);
(Continued)

(58) Field of Classification Search
None
See application file for complete search history.

(56) References Cited

U.S. PATENT DOCUMENTS 4,540,747 A    9/1985   Saegusa et al.
2014/0170197 A1   6/2014   Kabanov et al.

FOREIGN PATENT DOCUMENTS

CA    2197802 C  *  3/1996
DE    4403953 A1 *  8/1995
(Continued)

OTHER PUBLICATIONS

Schultz et al. (Drug-Induced Morphology Switch in Drug Delivery Systems Based on Poly(2-oxazoline)s, ACS Nano, Feb. 18, 2018, 38 pages.*
(Continued)

*Primary Examiner* — Tae H Yoon
(74) *Attorney, Agent, or Firm* — Kagan Binder, PLLC

(57) ABSTRACT

Provided is an (A)-(B)-(A) triblock copolymer comprising two hydrophilic polymer blocks (A) as further defined herein, and a polymer block (B), said polymer block (B) comprising at least one type of repeating unit of the following formula (I) wherein $R^1$ is an aliphatic hydrocarbon group which is optionally substituted with one or more of $-OR^5$, $-SR^5$, $-NR^6R^7$, $-(NR^6R^7R^8)+$, $-CONR^6R^7$, $-C(O)OR^9$ and $-C(O)R^{10}$, wherein $R^5$ to $R^{10}$ are independently selected from H, aliphatic and aromatic residues, and wherein $R^1$ is selected such that the polymer block (B) is more hydrophobic than the polymer block (A); and compositions, such as pharmaceutical compositions, formed with the block copolymer.

(Continued)

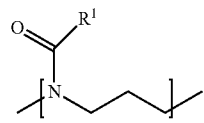

(I)

19 Claims, 8 Drawing Sheets

(51) Int. Cl.
  *C08F 291/12* (2006.01)
  *C08G 81/00* (2006.01)
  *C08L 79/02* (2006.01)
  *A61K 31/337* (2006.01)

(52) U.S. Cl.
  CPC ............. *C08G 73/02* (2013.01); *C08G 81/00* (2013.01); *C08L 79/02* (2013.01); *A61K 31/337* (2013.01)

(56) References Cited

FOREIGN PATENT DOCUMENTS

| EP | 0022148 | * | 1/1981 |
| JP | 2643403 B2 | * | 8/1997 |
| JP | 2007099930 A | * | 4/2007 |

OTHER PUBLICATIONS

International Search Report for International Application No. PCT/EP2018/066301, dated Sep. 10, 2018 (2 pages).

\* cited by examiner

BLOCK-COPOLYMERS FOR THE DELIVERY OF ACTIVE AGENTS

CROSS-REFERENCE TO RELATED APPLICATIONS

This application claims priority to International Application No. PCT/EP2018/066301, filed Jun. 19, 2018 and titled "BLOCK-COPOLYMERS FOR THE DELIVERY OF ACTIVE AGENTS," which in turn claims priority from a European Patent Application having Ser. No. 17/176,886.4, filed Jun. 20, 2017 and titled "BLOCK-COPOLYMERS FOR THE DELIVERY OF ACTIVE AGENTS," both of which are incorporated herein by reference in their entireties.

The present invention provides block copolymers which can be effectively used for the delivery of active agents in particular in aqueous environments.

Many of the most potent drugs and drug candidates are not water soluble. Formulation of poorly soluble drugs, such as paclitaxel (PTX) with a water solubility of approx. 1 µg/mL, remains a major challenge in drug delivery (Huh, K. M., et al., J. Controlled Release 126, 122-129 (2008); Dabholkar, R. D., et al. Int. J. Pharm. 315, 148-157 (2006); Yang, T., et al., Int. J. Pharm. 338, 317-326 (2007); Torchilin, V. P., Cell. Mol. Life. Sci 61, 2549-2559 (2004); Haag, R., Angew. Chem. Int. Ed. 43, 278-282 (2004)). The clinical formulation Taxol®, contains less than 1% w/w of PTX, but 99% w/w of excipients which potentially cause considerable side effects for the patients. Similar problems are encountered with active agents in other technical areas, such as plant protection, etc. Various methods to solubilize or disperse active agents have been developed. Traditional methods are typically based on the use of solvents, surfactants or chelating agents. These methods have one or more disadvantages related to toxicity of the excipients, limited stability of the formulations in aqueous media, in particular upon dilution, or difficult formulation procedures More recently, liposomes (Wu, J., et al., Int. J. Pharm. 316, 148-153 (2006)), micro- and nanoparticles (Desai, N. P. et al., Anti-Cancer Drugs 19, 899-909 (2008)) and polymer micelles (Huh, K. M., et al., J. Controlled Release 126, 122-129 (2008); Konno, T., et al., J. Biomed. Mat. Res., Part A, 65A, 210-215 (2002); Kim, S. C., et al., J. Controlled Release 72, 191-202 (2001)) have been studied intensively as solubilzation/drug delivery systems, each approach having advantages and disadvantages. One major limitation of many polymer micelles is the loading capacity and the total amount of drug that can be solubilized. U.S. Pat. App. 20040185101 discloses polymeric compositions with the capability to solubilize hydrophobic drugs in aqueous media. However, the loading capacity of these compositions is limited with a loading capacity of e.g. <10% (w/w) for paclitaxel, or less than 1% (w/w) for cyclosporin A. In WO 2009/156180, poly(2-oxazoline) based polymers are disclosed as excellent candidates for the formulation of active agents, in particular of active agents which are hardly soluble or practically insoluble in water.

U.S. Pat. No. 4,540,747 discloses block copolymers of poly(N-formylethyleneimine) or poly(N-acetylethyleneimine) with poly(N-acylethyleneimine or poly(N-acylpropyleneimine) which are useful as surface active agents. However, the diblock copolymers as shown in this document are not suitable to solubilize high concentrations of active agents with a low water solubility.

Thus, a need remains for solubilizing materials which provide stable formulations of active agents at a high loading capacity. The synthesis of such materials and the formulation process using them should be simple and reproducible, and to make them suitable for the preparation of pharmaceutical compositions, they should have no or no significant toxicity. The present inventors have found that the block copolymers provided herein have excellent characteristics as polymers for the delivery of active agents, and allow the preparation of stable compositions comprising large concentrations of such agents which surprisingly even exceed those demonstrated for the poly(2-oxazoline) based polymers of WO 2009/15680.

To that extent, the invention provides, in accordance with a first aspect, an (A)-(B)-(A) triblock copolymer comprising two hydrophilic polymer blocks (A), which are independently selected from:

(i) a polymer block (A) formed from at least one type of the repeating units of the following formula (II)

wherein $R^2$ is an aliphatic hydrocarbon group which is optionally substituted with one or more of $-OR^{11}$, $-SR^{11}$, $-NR^{11}R^{12}$, $-(NR^{11}R^{12}R^{13})^+$, $-CONR^{11}R^{12}$, $-C(O)OR^{14}$ and $-C(O)R^{15}$, wherein $R^{11}$ to $R^{15}$ are independently selected from H and C1-C3 alkyl, and wherein the aliphatic hydrocarbon group and the optional substituents are selected such that the resulting polymer block (A) is hydrophilic;

(ii) a polymer block (A) formed from at least one type of the repeating units of the following formula (III)

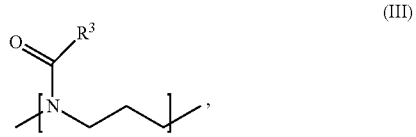

wherein $R^3$ is selected from a methyl and an ethyl group, which groups are optionally substituted with one or more of $-OR^{11}$, $-SR^{11}$, $-NR^{11}R^{12}$, $-(NR^{11}R^{12}R^{13})+$, $-CONR^{11}R^{12}$, $-C(O)OR^{14}$ and $-C(O)R^{15}$, wherein $R^{11}$ to $R^{15}$ are independently selected from H and C1-C3 alkyl and wherein the optional substituents, if present, are selected such that the resulting polymer block (A) is hydrophilic; and (iii) a polymer block (A) formed from at least one type of the repeating units of formula (II) and at least one type of the repeating units of formula (III) as defined above, and a polymer block (B), said polymer block (B) comprising at least one type of repeating unit of the following formula (I)

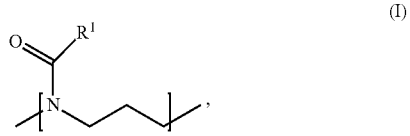

wherein $R^1$ is an aliphatic hydrocarbon group which is optionally substituted with one or more of $-OR^5$, $-SR^5$, $-NR^6R^7$, $-(NR^6R^7R^8)^+$, $-C(O)OR^9$, $-CONR^6R^7$ and $-C(O)R^{10}$, wherein $R^5$ to $R^{10}$ are independently selected from H, aliphatic or aromatic residues,
and wherein $R^1$ is selected such that the polymer block (B) is more hydrophobic than the polymer block (A).

The (A)-(B)-(A) triblock copolymer defined above is referred to herein also as the "block copolymer in accordance with the invention", or simply as the "copolymer in accordance with the invention.

In accordance with a further aspect, the invention provides compositions, such as pharmaceutical compositions, diagnostic compositions or compositions for plant protection, comprising one or more block copolymers in accordance with the invention in combination with one or more compounds to be solubilized. The pharmaceutical compositions can be suitably used to deliver a therapeutically active agent as a compound to be solubilized to a subject.

Thus, they also provide a basis for a method of treating a disorder in a patient, said method comprising the administration of such a pharmaceutical composition to a patient.

In accordance with still a further aspect, the invention relates to the use of one or more block copolymers in accordance with the invention for the solubilization of one or more compounds to be solubilized in an aqueous environment. Similarly, the invention encompasses a method for solubilizing one or more compounds to be solubilized, comprising the step of combining the compound(s) with one or more block copolymers in accordance with the invention.

As noted above, the block copolymer in accordance with the invention comprises two hydrophilic polymer blocks (A) and one polymer block (B), said polymer block (B) comprising at least one type of repeating unit of the following formula (I)

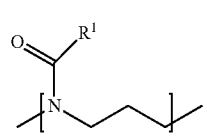

(I)

wherein $R^1$ is an aliphatic hydrocarbon group which is optionally substituted with one or more of $-OR^5$, $-SR^5$, $-NR^6R^7$, $-(NR^6R^7R^9)^+$, $-CONR^6R^7$, $-C(O)OR^9$ and $-C(O)R^{10}$, wherein $R^5$ to $R^{10}$ are independently selected from H, aliphatic and aromatic residues, and wherein $R^1$ is selected such that the polymer block (B) is more hydrophobic than the polymer block (A).

The term "block copolymer" is used herein in accordance with its established meaning in the art to refer to copolymers wherein repeating units of a defined type, e.g. hydrophilic repeating units and hydrophobic repeating units, are organized in blocks. Typically, the blocks (A) contained in the block copolymer in accordance with the invention can be considered as polymers themselves, and the same applies for the block (B). Thus, reference may be made herein to a "polymer A" providing the polymer blocks (A), and to a "polymer B" providing the polymer block (B) in the block copolymer in accordance with the invention. The terms "hydrophilic" and "hydrophobic" as used herein have a well recognized meaning in the art. "Hydrophilic" designates a preference of a substance or moiety for aqueous environments, i.e. a hydrophilic substance or moiety is more readily dissolved in or wetted by water than by non-polar solvents, such as hydrocarbons. "Hydrophobic" designates a preference for apolar environments i.e. a hydrophobic substance or moiety is more readily dissolved in or wetted by non-polar solvents, such as hydrocarbons, than by water.

A variety of monomers or polymers are available for the skilled person which are known as being hydrophilic, and which can be suitably used to provide a polymer A and thus a hydrophilic polymer block (A) for the block copolymer in accordance with the invention. It will also be possible for the skilled person, where necessary based on established tests, to select suitable monomers or polymers which are suitable to provide a polymer B which is more hydrophobic than a given polymer A. For example, in order to provide the hydrophilic polymer blocks (A), a hydrophilic polymer A is preferably used which (if prepared alone, i.e. in the absence of a block (B)) has a water solubility of at least 10 g/L, preferably at least 100 g/L at 293K. In order to provide the more hydrophobic block (B), a polymer B is preferably used which (if prepared alone, i.e. in the absence of a block (A)) has a water solubility of less than 10 g/L at 293K. It will be understood that the polymer block (B) is more hydrophobic than each of the polymer blocks (A).

The polymer blocks (A) are hydrophilic polymer blocks. The hydrophilic polymer blocks (A) may, independently for each polymer block (A), be selected from a poly(2-oxazoline) block, a poly(2-oxazine) block, or from a polymer block formed from 2-substituted oxazolines and 2-substituted oxazines (also referred to as 2-substituted 5,6-dihydro-4H-1,3-oxazines).

As regards a poly(2-oxazoline) block as polymer block (A), it will be understood that the term "poly(2-oxazoline)" as used herein refers to a polymer which may be formed by the cationic ring-opening polymerization of 2-oxazolines as monomers which carry a substituent on position 2, defined as a substituent $R^2$ herein. As will be understood by the skilled person, 2-substituted 2-oxazolines which are polymerized to provide a possible polymer block (A) in the copolymers in accordance with the invention carry a substituent on position 2 which leads to hydrophilic properties for block (A). In accordance with IUPAC nomenclature, the 2-substituted 2-oxazoline monomers forming the poly(2-oxazoline) are also referred to as 2-substituted 4,5-dihydro-oxazoles. A well known alternative term for poly(2-oxazoline)s is poly(N-acylethylene imine)s.

As regards a poly(2-oxazine) block as polymer block (A), it will be understood that the term "poly(2-oxazine)" as used herein refers to a polymer which may be formed by the cationic ring-opening polymerization of 2-oxazines as monomers which carry a substituent on position 2, defined as a substituent $R^3$ herein. As will be understood by the skilled person, 2-substituted 2-oxazines which are polymerized to provide a possible polymer block (A) in the copolymers in accordance with the invention carry a substituent on position 2 which leads to hydrophilic properties for block (A). In accordance with IUPAC nomenclature, the preferred substituted 2-oxazine monomers forming the poly (2-oxazine) are also referred to as 2-substituted 5,6-dihydro-4H-1,3-oxazines. An alternative term for poly(2-oxazines)s is poly(N-acylpropylene imine)s.

As noted above, the hydrophilic polymer blocks (A) are independently selected from the following (i) to (iii):
(i) a polymer block (A) formed from at least one type of the repeating units of the following formula (II)

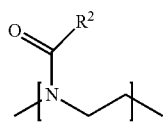

(II)

(i.e. a poly(2-oxazoline) block), wherein $R^2$ is an aliphatic hydrocarbon group which is optionally substituted with one or more of $-OR^{11}$, $-SR^{11}$, $-NR^{11}R^{12}$, $-(NR^{11}R^{12}R^{13})^+$, $-CONR^{11}R^{12}$, $-C(O)OR^{14}$ and $-C(O)R^{15}$, wherein $R^{11}$ to $R^{15}$ are independently selected from H and C1-C3 alkyl, and wherein the aliphatic hydrocarbon group and the optional substituents are selected such that the resulting polymer block (A) is hydrophilic;

(ii) a polymer block (A) formed from at least one type of the repeating units of the following formula (III)

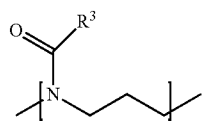

(III)

(i.e. a poly(2-oxazine) block) wherein $R^3$ is selected from a methyl and an ethyl group, which groups are optionally substituted with one or more of $-OR^{11}$, $-SR^{11}$, $-NR^{11}R^{12}$, $-(NR^{11}R^{12}R^{13})^+$, $-CONR^{11}R^{12}$, $-C(O)OR^{14}$ and $-C(O)R^{15}$, wherein $R^{11}$ to $R^{15}$ are independently selected from H and C1-C3 alkyl and wherein the optional substituents, if present, are selected such that the resulting polymer block (A) is hydrophilic; and (iii) a polymer block (A) formed from at least one type of the repeating units of formula (II) and at least one type of the repeating units of formula (III) as defined above.

Among these options, option (i) is preferred.

As will be understood, the hydrophilic property of the unit of formula (II) as defined above will depend on the size of the aliphatic hydrocarbon group in $R^2$. If a small hydrocarbon group is selected, such as methyl or ethyl, the resulting group $R^2$, unsubstituted or substituted with the above substituents, will generally result in a hydrophilic unit of formula (II). If a larger hydrocarbon group is selected, the presence of substituents may be advantageous to introduce additional polarity and thus hydrophilic properties to the unit of formula (II).

Further regarding formula (II), it is preferable that $R^2$ is an optionally substituted alkyl group, more preferably an optionally substituted C1-C6 alkyl group, and more preferably an optionally substituted methyl or ethyl group. An (optionally substituted) alkyl group as $R^2$ may be linear, branched or cyclic. Even more preferably, $R^2$ is a non-substituted methyl group or a non-substituted ethyl group, and most preferably a non-substituted methyl group.

As regards formula (III), it is preferred that $R^3$ is a non-substituted methyl group or a non-substituted ethyl group, and it is more preferred that $R^3$ is a non-substituted methyl group.

In line with conventional practice it will be understood that the brackets [ ] in the formulae indicate that the entity within the brackets (i.e. $-N(C(O)R^2)-CH_2-CH_2-$ for formula (II), and $-N(C(O)R^3)-CH_2-CH_2-CH_2-$ for formula (III)) represents a repeating unit of the polymer block, and the lines crossing the brackets indicate the bonds which link the repeating unit to adjacent atoms or entities, typically to an adjacent repeating unit of the same polymer block, to an adjacent repeating unit of a different polymer block, or to a terminal group of the block copolymer. The reference to a polymer block "formed from" an indicated repeating unit or a group of repeating units indicates that the polymer block consists of the respective units.

In view of the above explanations, it will be understood that in a strongly preferred embodiment, the hydrophilic polymer block(s) (A) is/are, independently for each polymer block (A) if more than one polymer block (A) is present, selected from (i) a polymer block (A) formed from at least one type of the repeating units of the formula (II) as shown above wherein $R^2$ is selected from a methyl and an ethyl group, and is more preferably a methyl group;

(ii) a polymer block (A) formed from at least one type of the repeating units of the formula (III) as shown above wherein $R^3$ is selected from a methyl and an ethyl group, and is more preferably a methyl group; and (iii) a polymer block (A) formed from at least one type of the repeating units of formula (II) as shown above, wherein $R^2$ is selected from a methyl and an ethyl group, and is more preferably a methyl group, and at least one type of the repeating units of formula (III) wherein $R^3$ is selected from a methyl and an ethyl group, and is more preferably a methyl group.

It will be understood that the structure of these preferred repeating units will in any case yield a hydrophilic polymer block.

Preferably, all repeating units within a polymer block (A) are the same, but the two polymer blocks (A) may be formed from different repeating units. More preferably, all repeating units within a polymer block (A) are the same, and the two polymer blocks (A) are also formed from the same repeating unit.

The number of repeating units forming the polymer blocks (A) is, independently for each polymer block (A) preferably 5 or more, more preferably 10 or more, and even more preferably 20 or more. It is generally 300 or less, preferably 200 or less, more preferably 100 or less and even more preferably 50 or less.

In line with the above, two preferred structures of the polymer blocks (A) are indicated by the following formulae (IIa) and (IIIa):

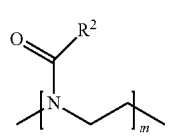

(IIa)

wherein $R^2$ is an alkyl group, preferably a C1-C6 alkyl group and more preferably methyl or ethyl, optionally substituted with one or more of $-OR^{11}$, $-SR^{11}$, $-(NR^{11}R^{12}R^{13})^+$, $-C(O)OR^{14}$ and $-C(O)R^{15}$, wherein $R^{11}$ to $R^{15}$ are independently selected from H and C1-C3 alkyl, and wherein the aliphatic hydrocarbon group and the optional substituents are selected such that the resulting polymer block (A) is hydrophilic. Even more preferably, $R^2$ is non-substituted methyl or ethyl, and most preferably non-substituted methyl. m is 10 or more, preferably 20 or more. It is generally 300 or less, preferably 200 or less, more preferably 100 or less and even more preferably 50 or less;

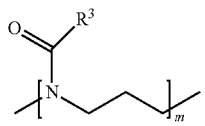

(IIIa)

wherein $R^3$ is selected from a methyl and an ethyl group, which groups are optionally substituted with one or more of —$OR^{11}$, —$SR^{11}$, —$NR^{11}R^{12}$, —$(NR^{11}R^{12}R^{13})^+$, —$CONR^{11}R^{12}$, —$C(O)OR^{14}$ and —$C(O)R^{15}$, wherein $R^{11}$ to $R^{15}$ are independently selected from H and C1-C3 alkyl and wherein the optional substituents, if present, are selected such that the resulting polymer block (A) is hydrophilic. More preferably, $R^3$ is a non-substituted methyl group or a non-substituted ethyl group, and it is still more preferred that $R^3$ is a non-substituted methyl group. m is 10 or more, preferably 20 or more. It is generally 300 or less, preferably 200 or less, more preferably 100 or less and even more preferably 50 or less.

Among them, polymer blocks of formula (IIa) are particularly preferred.

The polymer block (B) contained in the block copolymer in accordance with the invention comprises at least one type of repeating unit of the following formula (I)

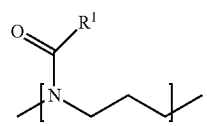

(I)

wherein $R^1$ is an aliphatic hydrocarbon group which is optionally substituted with one or more of —$OR^5$, —$SR^5$, —$NR^6R^7$, —$(NR^6R^7R^8)^+$, —$CONR^6R^7$, —$C(O)OR^9$ and —$C(O)R^{10}$, wherein $R^5$ to $R^{19}$ are independently selected from H, aliphatic and aromatic residues, typically aliphatic or aromatic hydrocarbon residues, and wherein $R^1$ is selected such that the polymer block (B) is more hydrophobic than the polymer block (A).

Preferably, $R^1$ in the repeating units of formula (I) is an optionally substituted aliphatic C3-C20 hydrocarbon group. More preferably, $R^1$ in the repeating units of formula (I) is an optionally substituted C3-C20 alkyl group. An (optionally substituted) alkyl group as $R^1$ may be linear, branched or cyclic. Even more preferably, $R^1$ in the repeating units of formula (I) is an optionally substituted C3-C9 alkyl group, and still more preferably an optionally substituted C3-C5 alkyl group. The alkyl group is preferably not substituted. Thus, still more preferably, $R^1$ is a non-substituted C3-C9 alkyl group, even more preferably a non-substituted C3-C5 alkyl group and most preferably a non-substituted propyl or a non-substituted butyl group, e.g. a n-propyl or n-butyl group.

As regards the optional substituent groups of $R^1$ defined above, it is preferred that $R^5$ to $R^{10}$, if present, are independently selected from H, C1-C20 aliphatic hydrocarbon residues and phenyl, more preferably from H, C1-C6 alkyl and phenyl.

Typically, the repeating units of formula (I) provide 50% or more of the repeating units of the polymer block (B), in terms of the number of repeating units of formula (I) with respect to the total number of repeating units in block (B) as 100%. The polymer block (B) may also be formed from the repeating units of formula (I), i.e. consist of these repeating units.

A preferred repeating unit that may optionally be co-polymerized with the repeating units of formula (I) to provide the polymer block (B) in the block copolymer in accordance with the invention is a repeating unit of the following formula (IV):

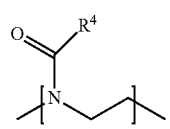

(IV)

wherein $R^4$ represents an alkyl group. The alkyl group may be linear, branched or cyclic. Preferably, R4 represents a C3-C20 alkyl group, more preferably a C3-C7 alkyl group, still more preferably a C3-C5 alkyl group, and most preferably a propyl or a butyl group, e.g. a n-propyl or n-butyl group.

Preferably, all repeating units within a polymer block (B) are the same.

In line with conventional practice it will be understood that the brackets [ ] in the formulae indicate that the entity within the brackets (i.e. —$N(C(O)R^1)$—$CH_2$—$CH_2$—$CH_2$— for formula (I) and —$N(C(O)R^4)$—$CH_2$—$CH_2$— for formula (IV)) represents a repeating unit of the polymer block, and the lines crossing the brackets indicate the bonds linking the repeating unit to adjacent atoms or entities, typically to a neighboring repeating unit of the same polymer block, to a neighboring repeating unit of a different polymer block, or to an end group of the block copolymer. The reference to a polymer block "formed from" an indicated repeating unit or a group of repeating units indicates that the polymer block consists of the respective units.

Thus, it is preferred that the polymer block (B) is selected from
 (i) a polymer block (B) formed from at least one type of the repeating units of formula (I) as shown above, wherein $R^1$ is a C3-C9 alkyl group, more preferably a C3-C5 alkyl group, and most preferably a propyl or butyl group, e.g. a n-propyl or n-butyl group, and
 (ii) a polymer block (B) formed from 50% or more, in terms of the number of repeating units and based on the total number of repeating units in the polymer block as 100%, of repeating units of formula (I) as shown above, wherein $R^1$ is a C3-C9 alkyl group, more preferably a C3-C5 alkyl group, and most preferably a propyl or butyl group, e.g. a n-propyl or n-butyl group, and 50% or less, in terms of the number of repeating units and based on the total number of repeating units in the polymer block as 100%, of repeating units of formula (IV) as shown above wherein $R^4$ represents a C3-C7 alkyl group, more preferably a C3-C5 alkyl group, and most preferably a propyl or a butyl group, e.g. a n-propyl or n-butyl group, and wherein the sum of the number of the repeating units of formula (I) and of formula (IV) is 100%.

The number of repeating units forming the polymer block (B) is preferably 5 or more, more preferably 10 or more, and even more preferably 15 or more. It is generally 300 or less, preferably 200 or less, more preferably 100 or less and even more preferably 50 or less.

In line with the above, a preferred structure of the polymer block(s) (B) is indicated by the following formula (Ia)

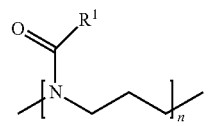

wherein $R^1$ is a C3-C9 alkyl group, more preferably a C3-C5 alkyl group, most preferably a propyl or butyl group, which is optionally substituted with one or more of $—OR^5$, $—SR^5$, $—NR^6R^7$, $—(NR^6R^7R^8)^+$, $—CONR^6R^7$, $—C(O)OR^9$ and $—C(O)R^{19}$, wherein $R^5$ to $R^{19}$ are independently selected from H, C1-C20 aliphatic hydrocarbon residues and phenyl, more preferably from H, C1-C6 alkyl and phenyl, and wherein $R^1$ is selected such that the polymer block (B) is more hydrophobic than the polymer block (A). Preferably, $R^1$ does not carry a substituent. n is 10 or more, preferably 15 or more. It is generally 300 or less, preferably 200 or less, more preferably 100 or less and even more preferably 50 or less.

Moreover, it will be understood from the above that it is preferred for the (A)-(B)-(A) triblock copolymer in accordance with the invention if
the hydrophilic polymer blocks (A) are independently selected from
(i) a polymer block (A) formed from at least one type of the repeating units of the formula (II) as shown above wherein $R^2$ is selected from a methyl and an ethyl group, and is more preferably a methyl group;
(ii) a polymer block (A) formed from at least one type of the repeating units of the formula (III) as shown above wherein $R^3$ is selected from a methyl and an ethyl group, and is more preferably a methyl group; and
(iii) a polymer block (A) formed from at least one type of the repeating units of formula (II) as shown above, wherein $R^2$ is selected from a methyl and an ethyl group, and is more preferably a methyl group, and at least one type of the repeating units of formula (III) wherein $R^3$ is selected from a methyl and an ethyl group, and is more preferably a methyl group; and
the polymer block (B) is selected from
(i) a polymer block (B) formed from at least one type of the repeating units of formula (I) as shown above, wherein $R^1$ is a C3-C9 alkyl group, more preferably a C3-C5 alkyl group, most preferably a propyl or butyl group, e.g. a n-propyl or n-butyl group, and
(ii) a polymer block (B) formed from 50% or more, in terms of the number of repeating units and based on the total number of repeating units in the polymer block as 100%, of repeating units of formula (I) as shown above, wherein $R^1$ is a C3-C9 alkyl group, more preferably a C3-C5 alkyl group, most preferably a propyl or butyl group, e.g. a n-propyl or n-butyl group, and 50% or less, in terms of the number of repeating units and based on the total number of repeating units in the polymer block as 100%, of repeating units of formula (IV) as shown above wherein $R^4$ represents a C3-C7 alkyl group, more preferably a C3-C5 alkyl group, most preferably a propyl or a butyl group, e.g. a n-propyl or n-butyl group, and wherein the sum of the number of the repeating units of formula (I) and of formula (IV) is 100%.

For the polymer blocks (A), option (i) is particularly preferred.

The block copolymer is a linear block copolymer having the triblock copolymer structure (A)-(B)-(A). As will be understood by the skilled reader, such an (A)-(B)-(A) triblock copolymer contains three polymer blocks, which polymer blocks are linearly arranged in the indicated order, i.e. a block (A) followed by a block (B) followed again by a block (A).

It is preferred that the two polymer blocks (A) contain similar numbers of repeating units, e.g. if the average number of repeating units is calculated, the number of repeating units in all polymer blocks (A) is within the range of the average number of repeating units ±50%, more preferably within the range of the average number of repeating units ±25%.

The ratio of repeating units contained in polymer blocks (A) to repeating units contained in polymer block (B), in terms of the numbers of repeating units, preferably ranges from 20:1 to 1:2, preferably from 10:1 to 1:1, more preferably from 7:1 to 2:1, and even more preferably from 7:1 to 3:1.

As apparent from the above, a preferred block copolymer in accordance with the invention is an (A)-(B)-(A) triblock copolymer, wherein
polymer blocks (A) are hydrophilic polymer blocks which are independently selected from
(i) a polymer block (A) formed from at least one type of the repeating units of the formula (II) as shown above wherein $R^2$ is selected from a methyl and an ethyl group, and is more preferably a methyl group;
(ii) a polymer block (A) formed from at least one type of the repeating units of the formula (III) as shown above wherein $R^3$ is selected from a methyl and an ethyl group, and is more preferably a methyl group; and
(iii) a polymer block (A) formed from at least one type of the repeating units of formula (II) as shown above, wherein $R^2$ is selected from a methyl and an ethyl group, and is more preferably a methyl group, and at least one type of the repeating units of formula (III) wherein $R^3$ is selected from a methyl and an ethyl group, and is more preferably a methyl group; and
polymer block (B) is selected from
(i) a polymer block (B) formed from at least one type of the repeating units of formula (I) as shown above, wherein $R^1$ is a C3-C9 alkyl group, more preferably a C3-C5 alkyl group, most preferably a propyl or butyl group, e.g. a n-propyl or n-butyl group, and
(ii) a polymer block (B) formed from 50% or more, in terms of the number of repeating units and based on the total number of repeating units in the polymer block as 100%, of repeating units of formula (I) as shown above, wherein $R^1$ is a C3-C9 alkyl group, more preferably a C3-C5 alkyl group, most preferably a propyl or butyl group, e.g. a n-propyl or n-butyl group, and 50% or less, in terms of the number of repeating units and based on the total number of repeating units in the polymer block as 100%, of repeating units of formula (IV) as shown above wherein $R^4$ represents a C3-C7 alkyl group, more preferably a C3-C5 alkyl group, most preferably a propyl or a butyl group, e.g. a n-propyl or n-butyl group, and wherein the sum of the number of the repeating units of formula (I) and of formula (IV) is 100%.

A more preferred block copolymer in accordance with the invention is an (A)-(B)-(A) triblock copolymer, wherein polymer blocks (A) are hydrophilic polymer blocks which are independently formed from at least one type of the repeating units of the formula (II) as shown above wherein R² is selected from a methyl and an ethyl group, and is more preferably a methyl group; and polymer block (B) is formed from at least one type of the repeating units of formula (I) as shown above, wherein R¹ is a C3-C5 alkyl group, more preferably a propyl or butyl group, e.g. a n-propyl or n-butyl group.

A particularly preferred block copolymer in accordance with the invention is an (A)-(B)-(A) triblock copolymer, wherein
the structure of the polymer blocks (A) is indicated, independently for each of the two polymer blocks, by the following formulae (IIa) or (IIIa)

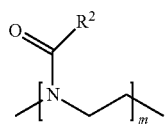
(IIa)

wherein,
R² is methyl or ethyl, more preferably methyl; and
m is 10 or more, preferably 20 or more, and is generally 300 or less, preferably 200 or less, more preferably 100 or less and even more preferably 50 or less;

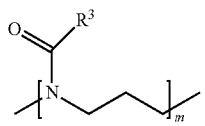
(IIIa)

wherein,
R³ is methyl or ethyl, more preferably methyl; and
m is 10 or more, preferably 20 or more, and is generally 300 or less, preferably 200 or less, more preferably 100 or less and even more preferably 50 or less;
the structure of the polymer block (B) is indicated by the following formula (Ia)

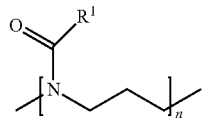
(Ia)

wherein R¹ is a C3-C9 alkyl group, preferably a C3-C5 alkyl group, most preferably propyl or butyl; such as n-propyl or n-butyl, and n is 10 or more, preferably 15 or more, and is generally 300 or less, preferably 200 or less, more preferably 100 or less and even more preferably 50 or less.

A still further preferred block copolymer in accordance with the invention is an (A)-(B)-(A) triblock copolymer, wherein
the structure of the polymer blocks (A) is indicated, independently for each of the two polymer blocks, by the following formula (IIa)

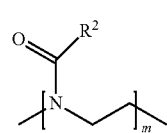
(IIa)

wherein,
R² is methyl or ethyl, more preferably methyl; and
m is 10 or more, preferably 20 or more, and is generally 300 or less, preferably 200 or less, more preferably 100 or less and even more preferably 50 or less; and
the structure of the polymer block (B) is indicated by the following formula (Ia)

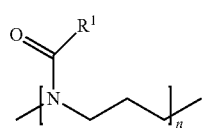
(Ia)

wherein R¹ is a C3-C5 alkyl group, more preferably propyl or butyl; such as n-propyl or n-butyl, and n is 10 or more, preferably 15 or more, and is generally 300 or less, preferably 200 or less, more preferably 100 or less and even more preferably 50 or less.

The block copolymers of the present invention can be prepared by polymerization methods known in the art. For example, a polymer block (B) can be conveniently prepared via cationic ring-opening polymerization of 2-substituted 2-oxazines (also referred to as 2-substituted 5,6-dihydro-4H-1,3-oxazines) of the formula

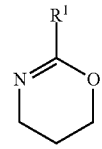

wherein R¹ is defined as above. Also, the combination of the polymer blocks (B) with polymer blocks (A) representing poly(2-oxazine) blocks or poly(2-oxazoline) blocks can be conveniently accomplished using cationic ring opening polymerization methods, e.g. using 2-substituted 2-oxazines of the formula

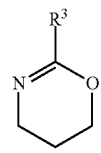

or 2-substituted 2-oxazolines of the formula

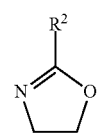

wherein $R^3$ and $R^2$ are defined as above. Suitable conditions for the cationic ring opening polymerization are disclosed, e.g., by R. Luxenhofer and R. Jordan, Macromolecules 39, 3509-3516 (2006), T. Bonne et al., Colloid. Polym. Sci., 282, 833-843 (2004) or T. Bonne et al. Macromol. Chem. Phys. 2008, 1402-1408, (2007).

As indicated above, also, within one block, 2-oxazines and 2-oxazolines with hydrophilic properties or 2-oxazines and 2-oxazolines with hydrophobic properties can be combined to give blocks formed from copolymers.

In accordance with a further aspect, the invention provides a composition comprising one or more block copolymers in accordance with the invention in combination with one or more compounds to be solubilized.

As will be understood by the skilled reader, the block copolymers are broadly applicable as materials for the delivery and/or solubilization of compounds, and the expression "to be solubilized" serves mainly as an illustration for the effect that can be exerted by the block copolymers without imposing a direct restriction on the type of compound or the properties thereof. However, the block copolymers are typically used in combination with compounds which are intended to be brought into contact with an aqueous environment, generally compounds which are to be at least partly dissolved or dispersed in such an aqueous environment, and which have a limited solubility in the aqueous environment or are even considered to be non-water soluble.

Therefore, the compound(s) to be solubilized can typically be characterized as compounds with a solubility in water (generally distilled water) at a temperature of 25° C. of preferably not more than 1 g/l, more preferably not more than 0.1 g/l, even more preferably not more than 0.01 g/l. The solubility can be determined, e.g., in accordance with the method disclosed in the European Pharmacopoeia, Version 7.0. Preferably, this limited solubility is shown also in water containing a Broensted acid or a base, across the pH range of 4 to 10.

Frequently, the compound(s) to be solubilized are solid compounds (at a temperature of 25° C.), prior to solubilization.

An aqueous environment as referred to herein is typically an aqueous liquid phase, or a hydrogel. The term "aqueous liquid phase" refers to a liquid phase comprising more than 50% (vol./vol.), preferably more than 80%, more preferably more than 90% of water, and even more preferably a liquid phase containing water as the only liquid component, based on the total volume of the liquid phase, and, where relevant, determined at 25° C. The aqueous liquid phase includes a solution, or the liquid phase of an emulsion or of a suspension. The term "hydrogel" as used herein refers to a composition comprising water absorbed in a polymer network in amounts that weight of the water in the hydrogel is larger than the weight of the polymer network.

However, it will be understood that the compositions in accordance with the invention can comprise an aqueous environment, but do not need to do so, since the advantages of the compositions includes the possibility of conveniently storing, transporting, delivering, etc. a compound to be solubilized in a form in which it can be readily introduced and thus made available in an aqueous environment.

In the compositions in accordance with the invention, the weight ratio of the weight of the compound(s) to be solubilized to the weight of the block copolymer(s) of the invention as defined above is preferably at least 0.1:1.0, more preferably at least 0.5:1.0, and even more preferably at least 0.7:1.0. It is generally not more than 2.0:1.0, frequently not more than 1.5:1.0.

The composition in accordance with the invention can be a solid composition, preferably a composition wherein the block copolymer(s) and the compound(s) to be solubilized form a solid solution.

For example, the solid composition can comprise micelles, typically dried micelles, which micelles are formed by the block copolymer(s) and which incorporate the compound(s) to be solubilized. It could be also a so-called solid dispersion, obtainable e.g. by melting the polymer and compound together.

The block copolymers of the invention allow the compositions to be lyophilized without compromising the activity and the stability of an active agent contained therein as the compound to be solubilized, and without the need for a cryoprotectant. Thus, powders, especially lyophilized powders, form a preferred embodiment of the solid compositions according to the invention. These powders may be conveniently reconstituted in water or aqueous solutions.

The composition in accordance with the invention can also be a solution, an emulsion or a suspension. Preferably, such a solution, emulsion or suspension is an aqueous solution, emulsion or suspension. Also in this context, the term "aqueous" refers to a liquid phase, i.e. as the liquid phase of the solution, the emulsion or the suspension, comprising more than 50% (vol./vol.), preferably more than 80%, more preferably more than 90% of water, and even more preferably a liquid phase containing water as the only liquid component, based on the total volume of the liquid phase, and, where relevant, determined at 25° C.

Preferably, the composition takes the form of a solution, more preferably an aqueous solution, wherein micelles or compound micelles, which are formed by the block copolymer(s) in accordance with the invention and which incorporate the compound(s) to be solubilized, are dissolved as a colloidal phase in the liquid phase.

In accordance with another preferred embodiment, the composition takes the form of an aqueous suspension wherein polymersomes which are formed by the block copolymer(s) in accordance with the invention and which incorporate the compound(s) to be solubilized are suspended in the in the liquid phase.

Due to the high solubilizing efficiency observed for the block copolymers described above, it is generally sufficient for compositions, in particular pharmaceutical compositions in accordance with the invention in the form of aqueous solutions, emulsions or suspensions, if the content of the copolymer ranges from concentrations as low as 1 mg/ml, preferably 10 mg/ml, to concentrations of 200 mg/ml, preferably to 50 mg/ml or 20 mg/ml. Since the copolymers are biocompatible, i.e. non-toxic, and undergo rapid renal clearance, high concentrations are not critical, but are generally not required.

The polymers according to the present invention may form micelles or compound micelles by themselves or alternatively only in combination with a compound to be solubilized. It is generally preferred that the block copolymer(s) form micelles in the compositions in accordance with the invention which incorporate the compound(s) to be solubilized. A micelle, as referred to herein, is generally an aggregate of the amphiphilic block copolymers of the invention presenting a hydrophilic corona formed by the hydrophilic parts of the copolymer and sequestering the hydrophobic parts of said amphiphilic copolymers in the interior of the micelle. Micelles according to the invention are three-dimensional entities. More specifically, micelles according to the invention form, for example, by self-aggregation of the amphiphilic block copolymers in hydrophilic, preferably aqueous solutions. Upon formation of the micelles, the hydrophilic regions of said amphiphilic copolymers are in contact with the surrounding solvent, whereas the hydrophobic regions are facing towards the centre of the micelle. In the context of the invention, the centre of a micelle typically incorporates the hydrophobic active agent. A micelle may also be referred to as a "polymeric nanoparticle" because of its size in the nanometer range and its constituents being of polymeric nature.

Micelles of variable size may be formed by the pharmaceutical compositions according to the invention, depending on factors such as the molecular weight of the copolymer used, or the drug load. Generally preferred are micelles within a size range, as determined e.g. via dynamic light scattering (DLS) of 5-500 nm. However, it is possible to advantageously form micelles with sizes ranging from 5 to 100 or even 10 to 50 nm, which are particularly suitable for intravenous administration. Advantageously, the micelles typically have narrow particle size distributions.

As the compound or compounds to be solubilized, compounds for diverse applications can be used. For example, the compound to be solubilized can be an active agent, preferably a bioactive agent. Active agents may be selected e.g. from therapeutically active agents, agents for use in diagnosis, fungicides, pesticides, insecticides, herbicides, further compounds suitable in the field of plant or crop protection such as phytohormones, and catalytically active compounds. As used herein, the term "active agent" also includes compounds to be screened as potential leads e.g. in the development of therapeutically active agents or plant protecting agents.

The compositions in accordance with the invention can consist of the one or more block copolymers in accordance with the invention and one or more compounds to be solubilized. However, the compositions can additionally comprise auxiliary agents, adjuvants, excipients, and/or solvents (in particular solvents that provide an aqueous solution as discussed above), as considered necessary or appropriate for the intended application by the skilled person.

The compositions in accordance with the invention can be conveniently prepared by combining the block copolymer(s) of the invention with the compound(s) to be solubilized. Generally, the production involves mixing of the block copolymer(s) of the invention with the compound(s) to be solubilized, optionally in a suitable solvent.

As noted above, the compound to be solubilized may be a therapeutically active agent. To that extent, the present invention also provides a method for the preparation of a pharmaceutical composition, said method comprising the step of combining a block copolymer in accordance with the invention with a therapeutically active agent.

For example, a composition according to the invention comprising micelles may be conveniently formed, e.g., by the thin film dissolution method. In this method, the block copolymer(s) and the compound(s) to be solubilized are dissolved in a common solvent, such as acetonitrile, ethanol or dimethylsulfoxide. After removal of the solvent (e.g. by a stream of inert gas, gentle heating and/or application of reduced pressure), films formed by the copolymer(s) and the compound(s) to be solubilized can be easily dissolved in water or aqueous solutions and may be tempered at increased temperatures. When the films are dissolved, the micelles, form. The stability of the micelles allows the resulting solutions to be dried to form a powder. For example, they can be freeze-dried, generally without the need for a cryoprotectant, and reconstituted in water or aqueous solutions without compromising loading capacities or particle integrity.

Due to a generally low glass transition temperature of the block copolymers in accordance with the invention, the polymers and the to-be-solubilized compound can also be processed via extrusion or injection molding methods at low or moderate temperatures. This allows the compositions to be provided which comprise temperature sensitive active agents as compounds to be solubilized.

As noted above, as the compound or compounds to be solubilized, compounds for diverse applications can be used. Thus, to the extent that the compound to be solubilized is an active agent, which may be selected from therapeutically active agents, agents for use in diagnosis, fungicides, pesticides, insecticides, herbicides, further compounds suitable in the field of plant or crop protection such as phytohormones, and catalytically active compounds, or a compound to be screened as potential lead e.g. in the development of therapeutically active agents or plant protecting agents, the present invention also provides the compositions for use in such applications, or methods and uses of the compositions in these applications.

For example, the present invention also provides the compositions in accordance with the invention, wherein the compound(s) to be solubilized comprise one or more therapeutically active agents (so that the composition is a pharmaceutical composition), for use in the treatment or prevention of a disease or disorder that can be treated or prevented with the active agent(s). Equally disclosed are a method of delivering a therapeutically active agent to a subject, said method comprising administering the compositions in accordance with the invention, wherein the compound(s) to be solubilized comprise one or more therapeutically active agents to said subject, and a method of treating or preventing a disease or disorder in a subject, said method comprising the administration of the compositions in accordance with the invention, wherein the compound(s) to be solubilized comprise one or more therapeutically active agents, to the subject. Furthermore, the invention encompasses the use of a block copolymer in accordance with the present invention for the preparation of a pharmaceutical composition.

As a further example, the present invention provides the compositions in accordance with the invention, wherein the compound(s) to be solubilized comprise one or more diagnostically active agents (so that the composition is a diagnostic composition), for use in a method of diagnosis of a disease or disorder practiced on the human or animal body. Similarly, the present invention provides an in-vitro method for the diagnosis of a disease or disorder comprising contacting the composition with a sample taken from the human or animal body.

As a further example, the present invention provides a method for protecting plants, said method comprising contacting a seed, a plant or an environment where a plant is to be grown with a composition in accordance with the invention wherein the compound(s) to be solubilized comprise one or more active compounds selected from fungicides, pesticides, insecticides, herbicides, and phytohormones. The invention also encompasses the use of a composition in accordance with the invention wherein the compound(s) to be solubilized comprise one or more active compounds selected from fungicides, pesticides, insecticides, herbicides, and phytohormones for the protection of plants.

As yet a further example, the present invention provides a method of catalyzing a reaction, comprising contacting at least one of the reactants with a composition in accordance with the invention wherein the compound(s) to be solubilized comprise one or more catalytically active compounds. The invention also encompasses the use of a composition in accordance with the invention wherein the compound(s) to be solubilized comprise one or more catalytically active compounds for catalysis.

As still a further example, the present invention provides a method for the detection of one or more compounds which interact with a target of interest in a screening test, said method comprising the steps of providing one or more compounds to be subjected to the detection method, separately incorporating the compound(s) as compounds to be solubilized each into a composition in accordance with the invention, and subjecting the compositions to the screening test.

As a further example, the invention provides the use of one or more block copolymer(s) in accordance with the invention for the solubilization of one or more compounds in an aqueous environment. As will be understood, for the compounds in the context of this aspect, the information provided above with respect to the compounds to be solubilized applies. Also regarding the aqueous environment, the explanation provided above applies. In a similar context, the invention provides a method for solubilizing one or more compounds in an aqueous environment, comprising the step of incorporating the compound(s) as compounds to be solubilized into a composition in accordance with the invention.

In a preferred embodiment, the compositions in accordance with the invention are pharmaceutical compositions comprising one or more therapeutically active agents as compound(s) to be solubilized. In line with the above, therapeutically active agents used as compounds to be solubilized are typically characterized by a solubility in water (generally distilled water) at a temperature of 25° C. of preferably not more than 1 g/l, more preferably not more than 0.1 g/l, even more preferably not more than 0.01 g/l. Frequently, the therapeutically active agent is a solid compound (at a temperature of 25° C.), prior to solubilzation.

As will be understood by the skilled reader, the term "therapeutically active agent" (also referred to as a drug herein) includes agents for the treatment of a disease or a disorder in a subject, as well as agents for the prevention of a disease or disorder in a subject. The subject is typically a human, but agents for veterinary use are also encompassed by the term.

Specific examples of the therapeutically active agents include, but are not limited to, drugs in the following categories: drugs acting at synaptic and neuroeffector junctional sites, drugs acting on the central nervous system, drugs that influence inflammatory responses, drugs that affect the composition of body fluids, drugs affecting renal function and electrolyte metabolism, cardiovascular drugs, drugs affecting gastrointestinal function, drugs affecting uterine motility, chemotherapeutic agents for hyperproliferative diseases, particularly cancer, chemotherapeutic agents for parasitic infections, chemotherapeutic agents for microbial diseases, antineoplastic agents, immunosuppressive agents, drugs affecting the blood and blood-forming organs, hormones and hormone antagonists, dermatological agents, heavy metal antagonists, vitamins and nutrients, vaccines, oligonucleotides and gene therapies. Specific drugs which may be mentioned as being suitable for use in the present invention include amphotericin B, nifedipine, griseofulvin, taxanes including paclitaxel and docetaxel, statins including atorvastatin, doxorubicin, daunomycin, indomethacin, ibuprofen, etoposide, cyclosporin A, vitamin E, curcuminoids including curcumin, and testosterone.

Due to the inherent versatility of the pharmaceutical compositions forming a preferred embodiment according to the invention as regards bioactive agents/compounds to be incorporated, it will be understood that the compositions can be formulated as being suitable for the treatment or prevention of a wide variety of diseases or disorders such as cancer, neurodegenerative diseases, hepato-biliary diseases, cardiovascular diseases or pulmonary diseases.

The pharmaceutical compositions can be formulated by techniques known to the person skilled in the art, such as the techniques published in Remington's Pharmaceutical Sciences, 20th Edition. The pharmaceutical compositions can be formulated as dosage forms for oral, parenteral, such as intramuscular, intravenous, subcutaneous, intradermal, intraarterial, rectal, topical, pulmonary or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions and solutions are a preferred dosage form for parenteral administration. Dosage forms for rectal and vaginal administration include suppositories and ovula. Dosage forms for pulmonary administration/pulmonary delivery can be administered via inhalation and insufflation, for example by a metered dose inhaler. Dosage forms for topical administration include creams, gels, ointments, salves, patches and transdermal delivery systems.

The pharmaceutical compositions according to the invention may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. Oral and parenteral, especially intravenous administration is generally preferred since the compositions according to the invention provide a sufficient solubility and bioavailability for these routes even when hydrophobic active agents are used.

If the pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions can be suitably buffered, if necessary. The preparation of suitable parenteral formulations under sterile conditions is readily accomplished by standard pharmaceutical techniques well known to those skilled in the art.

The pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain additional excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerine, and combinations thereof.

Alternatively, the pharmaceutical compositions can be administered in the form of a suppository or pessary, or it may be applied topically in the form of a gel, hydrogel, lotion, solution, cream, ointment or dusting powder. The compositions of the present invention may also be dermally or transdermally administered, for example, by the use of a skin patch.

The pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

In view of the advantageous solubilizing effects provided by the compositions according to the invention, it will be understood that they are preferably administered in forms and/or according to modes of administration which require solubility of the therapeutically and/or diagnostically active agent in water.

Typically, a physician will determine the actual dosage of the pharmaceutical compositions which will be most suitable for an individual subject. The specific dose level and frequency of dosage for any particular individual subject may be varied and will depend upon a variety of factors including the disorder or disease to be treated or prevented, the specific therapeutically and/or diagnostically active compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compositions according to the invention for administration to a human (of approximately 70 kg body weight) may be 0.1 µg to 10 g, preferably 0.1 mg to 0.5 g, based on the weight of the active agent (i.e. the drug) per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prevention, to which the compositions according to the invention are administered, is generally a mammal. In the context of this invention, it is particularly envisaged that mammals are to be treated, besides humans, which are economically or agronomically important. Non-limiting examples of agronomically important animals are sheep, cattle and pig, while, for example, cats and dogs may be considered as economically important animals. Preferably, the subject/patient is a human.

The term "treatment of a disorder or disease" as used herein is well known in the art. "Treatment of a disorder or disease" implies that a disorder or disease has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

Also the term "prevention of a disorder or disease" as used herein is well known in the art. For example, a patient/subject suspected of being prone to suffer from a disorder or disease as defined herein may, in particular, benefit from a prevention of the disorder or disease. Said subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in said patient/subject (for example, said patient/subject does not show any clinical or pathological symptoms). Thus, the term "prevention" comprises the use of compounds of the present invention before any clinical and/or pathological symptoms are diagnosed or determined or can be diagnosed or determined by the attending physician.

In this specification, a number of documents, including journal articles and patents, is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

In the following items, important aspects of the invention are additionally summarized:

1. An (A)-(B)-(A) triblock copolymer comprising two hydrophilic polymer blocks (A), which are independently selected from (i) to (iii):

(i) a polymer block (A) formed from at least one type of the repeating units of the following formula (II)

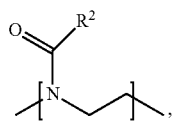

(II)

wherein $R^2$ is an aliphatic hydrocarbon group which is optionally substituted with one or more of $-OR^{11}$, $-SR^{11}$, $-NR^{11}R^{12}$, $-(NR^{11}R^{12}R^{13})+$, $-CONR^{11}R^{12}$, $-C(O)OR^{14}$ and $-C(O)R^{15}$, wherein $R^{11}$ to $R^{15}$ are independently selected from H and C1-C3 alkyl, and wherein the aliphatic hydrocarbon group and the optional substituents are selected such that the resulting polymer block (A) is hydrophilic;

(ii) a polymer block (A) formed from at least one type of the repeating units of the following formula (III)

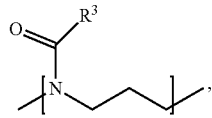

(III)

wherein $R^3$ is selected from a methyl and an ethyl group, which groups are optionally substituted with one or more of $-OR^{11}$, $-SR^{11}$, $-NR^{11}R^{12}$, $-(NR^{11}R^{12}R^{13})+$, $-CONR^{11}R^{12}$, $-C(O)OR^{14}$ and $-C(O)R^{15}$, wherein $R^{11}$ to $R^{15}$ are independently selected from H and C1-C3 alkyl and wherein the optional substituents, if present, are selected such that the resulting polymer block (A) is hydrophilic; and (iii) a polymer block (A) formed from at least one type of the repeating units of formula (II) and at least one type of the repeating units of formula (III) as defined above, and a polymer block (B), said polymer block (B) comprising at least one type of repeating unit of the following formula (I)

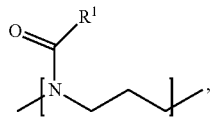

(I)

wherein $R^1$ is an aliphatic hydrocarbon group which is optionally substituted with one or more of $-OR^5$, $-SR^5$, $-NR^6R^7$, $-(NR^6R^7R^8)+$, $-C(O)OR^9$, $-CONR^6R^7$ and $-C(O)R^{10}$, wherein $R^5$ to $R^{19}$ are independently selected from H, aliphatic or aromatic residues, and wherein $R^1$ is selected such that the polymer block (B) is more hydrophobic than the polymer block (A).

2. The triblock copolymer of item 1, wherein the hydrophilic polymer blocks (A) are independently formed from at least one type of the repeating units of the following formula (II)

(II)

wherein $R^2$ is an aliphatic hydrocarbon group which is optionally substituted with one or more of $-OR^{11}$, $-SR^{11}$, $-NR^{11}R^{12}$, $-(NR^{11}R^{12}R^{13})+$, $-CONR^{11}R^{12}$, $-C(O)OR^{14}$ and $-C(O)R^{15}$, wherein $R^{11}$ to $R^{15}$ are independently selected from H and C1-C3 alkyl.

3. The triblock copolymer of item 1 or 2, wherein $R^2$ is an optionally substituted alkyl group.

4. The triblock copolymer of item 3, wherein $R^2$ is an optionally substituted methyl or ethyl group.

5. The triblock copolymer of any of items 2 to 4, wherein $R^2$ is a non-substituted methyl group or a non-substituted ethyl group, and more preferably a non-substituted methyl group.

6. The triblock copolymer of item 1 or 3 to 5, wherein $R^3$ is a non-substituted methyl group or a non-substituted ethyl group, and more preferably a non-substituted methyl group.

7. The triblock copolymer of any of items 1 to 6, wherein $R^1$ in the repeating units of formula (I) is an optionally substituted aliphatic C3-C20 hydrocarbon group.

8. The triblock copolymer of any of items 1 to 7, wherein $R^1$ in the repeating units of formula (I) is an optionally substituted C3-C20 alkyl group.

9. The triblock copolymer of any of items 1 to 8, wherein $R^1$ in the repeating units of formula (I) is an optionally substituted C3-C9 alkyl group.

10. The triblock copolymer of any of items 1 to 9, wherein $R^1$ in the repeating units of formula (I) is an optionally substituted C3-C5 alkyl group.

11. The triblock copolymer of any of items 1 to 10, wherein $R^1$ in the repeating units of formula (I) is a propyl or a butyl group.

12. The triblock copolymer of any of items 1 to 11, wherein the repeating units of formula (I) provide 50% or more of the repeating units of the polymer block (B), in terms of the number of repeating units of formula (I) with respect to the total number of repeating units in the block (B) as 100%.

13. The triblock copolymer of any of items 1 to 12, wherein the polymer block (B) further comprises a repeating unit of the following formula (IV)

(IV)

wherein $R^4$ represents an alkyl group, preferably a C3-C20 alkyl group, more preferably a C3-C7 alkyl group, still more preferably a C3-C5 alkyl group, and most preferably a propyl or a butyl group.

14. The triblock copolymer of any of items 1 to 13, wherein the polymer block (B) is selected from
(i) a polymer block (B) formed from at least one type of the repeating units of formula (I)

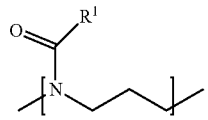

wherein $R^1$ represents a C3-C9 alkyl group, more preferably a C3-C5 alkyl group, and most preferably a propyl or butyl group; and
(ii) a polymer block (B) formed from 50% or more, in terms of the number of repeating units and based on the total number of repeating units in the polymer block as 100%, of repeating units of formula (I) as shown above, wherein $R^1$ represents a C3-C9 alkyl group, more preferably a C3-C5 alkyl group, and most preferably a propyl or butyl group, and 50% or less, in terms of the number of repeating units and based on the total number of repeating units in the polymer block as 100%, of repeating units of formula (IV)

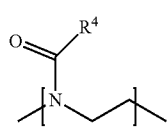

wherein $R^4$ represents a C3-C7 alkyl group, more preferably a C3-C5 alkyl group, and most preferably a propyl or a butyl group, e.g. a n-propyl or n-butyl group, and wherein the sum of the number of the repeating units of formula (I) and of formula (IV) is 100%.

15. The triblock copolymer of any of items 1 to 14, wherein the polymer block (B) is formed from at least one type of the repeating units of formula (I)

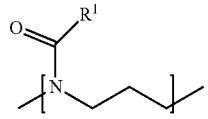

wherein $R^1$ represents a C3-C9 alkyl group, more preferably a C3-C5 alkyl group, and most preferably a propyl or butyl group.

16. The triblock copolymer of any of items 1 to 15, wherein the polymer blocks (A) and the polymer block (B) are each formed from a single type of repeating unit.

17. A composition comprising one or more triblock copolymers as defined in any of items 1 to 16 in combination with one or more compounds to be solubilized.

18. The composition of item 17, wherein the one or more compounds to be solubilized are characterized by a solubility in distilled water at a temperature of 25° C. of not more than 1 g/l, more preferably not more than 0.1 g/l, and even more preferably not more than 0.01 g/l.

19. The composition of item 17 or 18, wherein the weight ratio of the weight of the compound(s) to be solubilized to the weight of the triblock copolymer(s) is at least 0.1:1.0, more preferably at least 0.5:1.0 even more preferably at least 0.7:1.0.

20. The composition of any of items 17 to 19, which is a solid composition.

21. The composition of item 20, wherein the triblock copolymer(s) and the compound(s) to be solubilized form a solid solution.

22. The composition of any of items 17 to 19, which is a solution, an emulsion or a suspension.

23. The composition of item 22, which is an aqueous solution, aqueous emulsion or aqueous suspension.

24. The composition of item 22 or 23, wherein the composition comprises micelles which are formed by the triblock copolymer(s) and which incorporate the compound(s) to be solubilized.

25. The composition in accordance with any of items 17 to 19, wherein the one or more triblock copolymers form micelles which incorporate the compound(s) to be solubilized.

26. The composition in accordance with any of items 17 to 25, wherein the one or more compounds to be solubilized are active agents, more preferably bioactive agents.

27. The composition in accordance with any of items 17 to 26, wherein the one or more compounds to be solubilized are selected from therapeutically active agents, agents for use in diagnosis, fungicides, pesticides, insecticides, herbicides, phytohormones and catalytically active compounds.

28. The composition in accordance with any of items 17 to 27, which is a pharmaceutical composition which comprises one or more therapeutically active agents as the compound(s) to be solubilized.

29. The composition in accordance with item 28, wherein the therapeutically active agent comprises a chemotherapeutic agent which is suitable for the treatment of cancer.

30. A composition in accordance with item 29 for use in the treatment of cancer.

31. A method of delivering a therapeutically active agent to a subject, said method comprising administering the composition of any of items 28 to 30 to said subject.

32. A method of treating or preventing a disease or disorder in a subject, said method comprising the administration of the pharmaceutical composition of item 28 to the subject.

33. The method of item 32, wherein the disorder is cancer and wherein the therapeutically active agent comprises a chemotherapeutic agent which is suitable for the treatment of cancer.

34. Use of a triblock copolymer in accordance with any of items 1 to 16 for the preparation of a pharmaceutical composition comprising one or more therapeutically active agents as compounds to be solubilized.

35. A method for the preparation of a pharmaceutical composition, said method comprising the step of combining a triblock copolymer in accordance with any of items 1 to 16 with one or more therapeutically active agent as compounds to be solubilized.

36. Use of one or more triblock copolymers as defined in any one of items 1 to 16 for the solubilization of one or more compounds in an aqueous environment.

37. A method for solubilizing one or more compounds in an aqueous environment, comprising the step of incorporating the compound(s) as compounds to be solubilized into a composition in accordance with in any of items 17 to 27.

38. The use or method in accordance with item 36 or 37, wherein the aqueous environment comprises a liquid phase with a content of water of more than 50% (vol./vol.) or a hydrogel.

39. A method for the detection of one or more compounds which interact with a target of interest in a screening test, said method comprising the steps of providing one or more compounds to be subjected to the detection method, separately incorporating the compound(s) as compounds to be solubilized each into a composition as defined in any of items 17 to 26, and subjecting the compositions to the screening test.

40. The use or method of any of items 34 to 39, wherein the one or more compounds are characterized by a solubility in distilled water at a temperature of 25° C. of not more than 1 g/1, more preferably not more than 0.1 g/1, and even more preferably not more than 0.01 g/1.

Abbreviations which are used herein, especially in the experimental section are explained in the following
ACN acetonitrile
Ator atorvastatin
a.u. arbitrary units
BOC tert-butyloxycarbonyl
BOC-Pip 1-BOC-piperazine
$b_p$ boiling point
BuOx 2-n-butyl-2-oxazoline
BuOzi 2-n-butyl-2-oxazine
$CHCl_3$ chloroform
CMC critical micelle concentration
CP cloud point
cPrOx 2-cyclopropyl-2-oxazoline
cPrOzi 2-cyclopropyl-2-oxazine
CUR curcumin
d days
Đ dispersity (determined by GPC)
DLS dynamic light scattering
DP degree of polymerization
EtHepOx 2-(3-ethylheptyl)-2-oxazoline
EtHepOzi 2-(3-ethylheptyl)-2-oxazine
GPC gel permeation chromatography
HLB hydrophilic/lipophilic balance
HPLC high performance liquid chromatography
iPrOzi 2-isopropyl-2-oxazine
LC loading capacity ($m_{drug}/(m_{drug}+m_{polymer})*100\%$)
LCROP living cationic ring-opening polymerization
LCST lower critical solution temperature
LE loading efficiency ($m_{drug,\ solubilized}/m_{drug,\ added}*100\%$)
Me methyl
MeOH methanol
MeOTf methyltriflate
MeOx 2-methyl-2-oxazoline
MeOzi 2-methyl-2-oxazine
NMR nuclear magnetic resonance (spectroscopy)
In this context:

| s | singlet | m | multiplett |
|---|---------|----|------------|
| d | dublett | br | broad |
| t | triplett | | |
| q | quartett | | |

NonOx 2-n-nonyl-2-oxazoline
NonOzi 2-n-nonyl-2-oxazine
Ox 2-oxazoline; unspecified substituent at 2-position (according to the Hantzsch-Widmann-Patterson nomenclature for heterocyclic systems) systematic IUPAC name: 4,5-dihydrooxazole
Ozi 2-oxazine; unspecified substituent at 2-position (according to the Hantzsch-Widmann-Patterson nomenclature for heterocyclic systems) systematic IUPAC name: 5,6-dihydro-4H-1,3-oxazine
PDI polydispersity index (of aggregates determined by DLS)
PEG poly(ethylene glycol)
Pip piperazine
PipBoc tert-butyl piperazine-1-carboxylate (1-Boc-piperazine)
PhCl phenyl chloride
POx poly(2-oxazoline); unspecified substituent at 2-position
POzi poly(2-oxazine); unspecified substituent at 2-position
PPO poly(propylene oxide)
Prop propargyl group
PrOx 2-n-propyl-2-oxazoline
PrOzi 2-n-propyl-2-oxazine
PTX paclitaxel
PVP poly(vinyl pyrrolidone)
SD standard deviation
secBuOx 2-sec-butyl-2-oxazoline
SEM standard error mean
SLS static light scattering

EXAMPLES

Reagents and Solvents

All substances for the preparation of the polymers were purchased from Sigma-Aldrich (Steinheim, Germany) or Acros (Geel, Belgium) and were used as received unless otherwise stated. Curcumin powder from *Curcuma longa* (Turmeric) (curcumin ≥65%; (curcumin=79%; demethoxy-curcumin=17%, bisdemethoxycurcumin=4%; determined by HPLC)) and Atorvastatin calcium salt trihydrate 98%; HPLC) were purchased from Sigma-Aldrich. Paclitaxel was purchased from LC Laboratories (Woburn, MA, USA). Deuterated solvents for NMR analysis were obtained from Deutero GmbH (Kastellaun, Germany).

The monomers BuOx, BuOzi and PrOzi were prepared following the procedure by Seeliger et al. (H. Witte, W. Seeliger, Justus Liebigs Annalen der Chemie 1974, 1974, 996-1009). The monomers EtHepOx and EtHepOzi were prepared following the procedure by Kempe et al. (K. Kempe, S. Jacobs, H. M. L. Lambermont-Thijs, M. M. W. M. Fijten, R. Hoogenboom, U. S. Schubert, Macromolecules 2010, 43, 4098-4104). The monomers NonOx and NonOzi were prepared following the procedure by M. Beck et al. (M. Beck, P. Birnbrich, U. Eicken, H. Fischer, W. E. Fristad, B. Hase, H.-J. Krause, Die Angewandte Makromolekulare Chemie 1994, 223, 217-233).

All substances used for polymerization, methyl trifluoromethylsufonate (MeOTf), propargyl p-toluenesulfonate, MeOx, BuOx, PrOzi, BuOzi, EtHepOx, EtHepOzi, NonOx, NonOzi, benzonitrile (PhCN), sulfolane, acetonitrile, and other solvents for polymer preparation were refluxed over $CaH_2$ and distilled under argon.

Syntheses
Living Cationic Ring-Opening Polymerization, General Synthetic Procedure 1 (GSP1)

The polymerizations and work-up procedures were carried out as described previously (R. Luxenhofer, R. Jordan, Macromolecules 2006, 39, 3509-3516). Exemplary, the preparation of Prop-MeOx$_{35}$-b-PrOzi$_{20}$-b-MeOx$_{35}$-PipBoc was performed as follows:

Prop-MeOx$_{35}$-b-PrOzi$_{20}$-b-MeOx$_{35}$-PipBoc

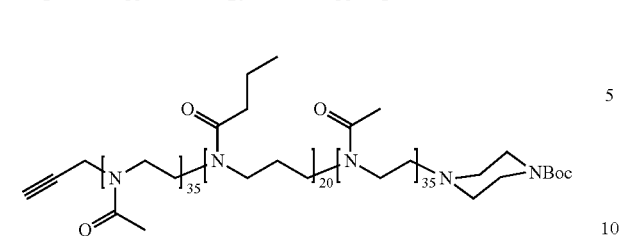

Under dry and inert conditions, 0.37 g (1.75 mmol, 1 eq) propargyl p-toluenesulfonate and 5.19 g (61.0 mmol, 35 eq) 2-methyl-2-oxazoline (MeOx) were dissolved in 35 mL dry sulfolane at room temperature. The mixture was stirred for 16 h at 90° C. After cooling to RT, the monomer for the second block, 2-n-propyl-2-oxazine (4.41 g, 34.7 mmol, 20 eq) was added and the mixture was stirred for 20 h at 100° C. The procedure was repeated for the third block with 5.19 g (70.0 mmol, 35 eq) MeOx. Termination was carried out with 0.97 g of 1-BOC-piperazine (5.23 mmol, 3 eq) at 50° C. overnight. K$_2$CO$_3$ (0.24 g, 1.74 mmol, 1 eq) was added and the mixture was stirred at 50° C. overnight. Precipitates were removed by centrifugation. The supernatant was transferred into a dialysis bag (MWCO 1 kDa) and dialyzed against Millipore water (1 L) overnight. The solution was recovered from the bag and lyophilized.

| | |
|---|---|
| Yield | 10.2 g (1.17 mmol; 67%) of a white powder |
| M | 8.7 kg/mol |
| GPC (DMF) | $M_n$ = 6.1 kg/mol; Đ (dispersity, determined via GPC) = 1.16 |
| $^1$H-NMR | $M_n$ = 9.8 kg/mol (Prop-MeOx$_{38}$-b-PrOzi$_{23}$-b-MeOx$_{38}$-PipBoc) (CDCl$_3$, 300.12 MHz; 298K): δ = 4.33-4.02 (br, 2H, alkyne-CH$_2$—N); 3.70-3.37 (br, 319H, (N—CH$_2$CH$_2$); 3.37-3.15 (br, 102H, N—CH$_2$—CH$_2$—CH$_2$—); 2.56-2.34 (br, 4H, pip—CH$_2$—CH$_2$—); 2.32-2.19 (br, 39H, CO—CH$_2$—CH$_2$—CH$_3$); 2.19-1.99 (br, 230H, CO—CH$_3$); 1.95-1.55 (br, 163H, N—CH$_2$—CH$_2$—CH$_2$—; CO—CH$_2$—CH$_2$—CH$_3$); 1.04-0.87 (br, 70H, CO—CH$_2$—CH$_2$—CH$_3$). |

Prop-MeOx$_{35}$-b-BuOzi$_{20}$-b-MeOx$_{35}$-PipBoc

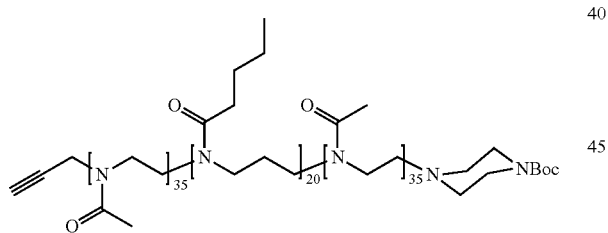

Prop-MeOx$_{35}$-b-BuOzi$_{20}$-b-MeOx$_{35}$-PipBoc was synthesized according to GSP 1

| | | | |
|---|---|---|---|
| Initiation: | PrOTs | 1.10 g | (5.22 mmol; 1 eq) |
| 1. Block: | MeOx | 15.6 g | (0.18 mol; 35 eq) |
| 2. Block: | BuOzi | 13.3 g | (0.10 mol; 20 eq) |
| 3. Block: | MeOx | 15.5 g | (0.18 mol; 35 eq) |
| Termination: | Boc-Pip | 3.0 g | (16.1 mmol; 3 eq) |
| Solvent | Sulfolane | 120 mL | |
| Yield | 31.4 g (3.5 mmol; 69%) of a white powder | | |
| M | 9.0 kg/mol | | |
| GPC (DMF) | $M_n$ = 5.6 kg/mol; Đ = 1.20 | | |
| $^1$H-NMR | $M_n$ = 13.3 kg/mol (Prop-MeOx$_{52}$-b-BuOzi$_{30}$-b-MeOx$_{52}$-PipBoc) (CDCl$_3$, 300.12 MHz; 298K): δ = 4.30-4.00 (br, 2H, alkyne-CH$_2$—N); 3.85-3.36 (br, 419H, (N—CH$_2$CH$_2$); 3.36-2.94 (br, 134H, N—CH$_2$—CH$_2$—CH$_2$—); 2.38-2.16 (br, 103H, CO—CH$_2$—CH$_2$—CH$_2$—CH$_3$); 2.17-1.92 (br, 310H, CO—CH$_3$); 1.92-1.67 (br, 50H, N—CH$_2$—CH$_2$—CH$_2$—); 1.67-1.46 (br, 57H, CO—CH$_2$—CH$_2$—CH$_2$—CH$_3$); 1.40-1.89 (br, 60H, CO—(CH$_2$)$_2$—CH$_2$—CH$_3$); 1.00-0.76 (br, 90H, CO—(CH$_2$)$_3$—CH$_3$). | | |

Prop-MeOx$_{35}$-b-BuOx$_{20}$-b-MeOx$_{35}$-Pip (Reference Polymer)

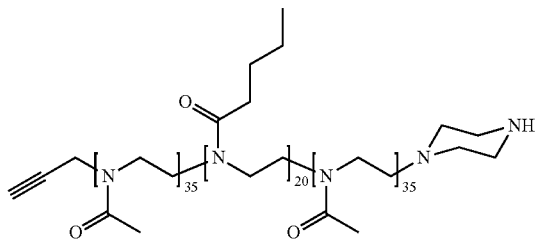

Prop-MeOx$_{35}$-b-BuOx$_{20}$-b-MeOx$_{35}$-Pip was synthesized according to GSP 1

| Initiation: | PrOTs | 0.38 g | (1.77 mmol; 1 eq) |
|---|---|---|---|
| 1. Block: | MeOx | 5.35 g | (6.18 mol; 35 eq) |
| 2. Block: | BuOx | 4.59 g | (3.53 mol; 20 eq) |
| 3. Block: | MeOx | 5.34 g | (6.18 mol; 35 eq) |
| Termination: | Pip | 3.04 g | (1.77 mmol; 3 eq) |
| Solvent | PhCl/ACN = 1/1 (v/v) | | 120 mL |
| Yield | 12.3 g (0.14 mmol; 82%) of a white powder | | |
| M | 8.5 kg/mol | | |
| GPC (DMF) | $M_n$ = 5.8 kg/mol; Đ = 1.19 | | |
| $^1$H-NMR | $M_n$ = 11.6 kg/mol (Prop-MeOx$_{45}$-b-BuOx$_{30}$-b-MeOx$_{45}$-Pip) (CDCl$_3$, 300.12 MHz; 298K): δ = 4.30-4.00 (br, 2H, alkyne-CH$_2$—N); 3.85-3.36 (br, 482H, (N—CH$_2$CH$_2$); 2.39-1.90 (br, 355H, CO—CH$_3$; CO—CH$_2$—(CH$_2$)$_2$—CH$_3$); 1.65-1.46 (br, 58H, CO—CH$_2$—CH$_2$—CH$_2$—CH$_3$); 1.40-1.26 (br, 59H, CO—(CH$_2$)$_2$—CH$_2$—CH$_3$); 0.97-0.83 (br, 89H, CO—(CH$_2$)$_3$—CH$_3$). | | |

Me-MeOzi$_{36}$-PrOzi$_{18}$-MeOzi$_{36}$-PipBoc

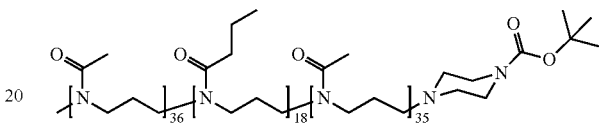

Me-MeOzi$_{36}$-PrOzi$_{18}$-MeOzi$_{35}$-PipBoc was synthesized according to GSP 1

| Initiation: | MeOTf | 0.06 g | (0.35 mmol; 1 eq) |
|---|---|---|---|
| 1. Block: | MeOzi | 1.25 g | (12.6 mmol; 36 eq) |
| 2. Block: | PrOzi | 0.81 g | (6.37 mmol; 18 eq) |
| 3. Block: | MeOzi | 1.22 g | (12.3 mmol; 35 eq) |
| Termination: | PipBoc | 0.20 g | (1.05 mmol; 3 eq) |
| Solvent | PhCN | 7 mL | |
| Yield | 2.02 g (0.21 mmol; 59%) of a white powder | | |
| M | 9.5 kg/mol | | |
| GPC (HFIP) | $M_n$ = 5.6 kg/mol; Đ = 1.29 | | |
| $^1$H-NMR | $M_n$ = 11.0 kg/mol (Me-MeOzi$_{41}$-b-PrOzi$_{21}$-b-MeOzi$_{41}$-PipBoc) (CDCl$_3$, 300.12 MHz; 298K): δ = 3.55-3.12 (br, 397H, N—CH$_2$—CH$_2$—CH$_2$); 3.04-3.00 (br, 3H, CH$_3$—N); 2.31-2.17 (br, 44H, CO—CH$_2$—CH$_2$—CH$_3$); 2.17-2.00 (br, 247H, CO—CH$_3$); 1.93-1.53 (br, 243H, CO—CH$_2$—CH$_2$—CH$_2$—CH$_3$; N—CH$_2$—CH$_2$—CH$_2$); 1.46-1.41 (br, 6H, -PipBoc); 1.00-0.84 (br, 62H, CO—(CH$_2$)2—CH$_3$). | | |

Me-MeOx$_{35}$-NonOx$_{12}$-MeOx$_{35}$-PipBoc (Reference Polymer)

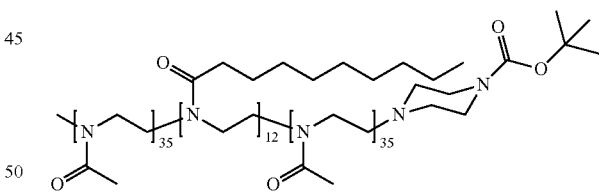

Me-MeOx$_{35}$-NonOx$_{12}$-MeOx$_{35}$-PipBoc was synthesized according to GSP 1

| Initiation: | MeOTf | 0.15 g | (0.9 mmol; 1 eq) |
|---|---|---|---|
| 1. Block: | MeOx | 2.69 g | (31.9 mol; 35 eq) |
| 2. Block: | NonOx | 2.14 g | (10.9 mol; 12 eq) |
| 3. Block: | MeOx | 2.68 g | (31.5 mol; 35 eq) |
| Termination: | PipBoc | 0.51 g | (2.7 mmol; 3 eq) |
| Solvent | PhCN | 16 mL | |
| Yield: | 6.47 g (0.76 mmol; 84%) of a white powder | | |
| M | 8.5 kg/mol | | |
| GPC (HFIP) | $M_n$ = 5.1 kg/mol; Đ = 1.16 | | |
| $^1$H-NMR | $M_n$ = 8.3 kg/mol (Me-MeOx$_{33}$-b-NonOx$_{11}$-b-MeOx$_{33}$-PipBoc) (CDCl$_3$, 300.12 MHz; 298K): δ = 3.58-3.31 (br, 305H, N—CH$_2$—CH$_2$); 3.07-2.93 (br, 3H, CH$_3$—N); 2.37-2.18 (br, 23H, CO—CH$_2$—(CH$_2$)$_7$—CH$_3$); 2.18-1.98 (br, 199H, CO—CH$_3$); 1.67-1.49 (br, 23H, | | |

CO—CH$_2$—CH$_2$—(CH$_2$)$_6$—CH$_3$); 1.48-1.42 (br, 10H, -PipBoc); 1.36-1.15 (br, 137H, CO—(CH$_2$)$_2$—(CH$_2$)$_6$—CH$_3$; 0.92-0.80 (br, 34H, CO—(CH$_2$)$_8$—CH$_3$).

Me-MeOx$_{35}$-NonOzi$_{11}$-MeOx$_{35}$-PipBoc

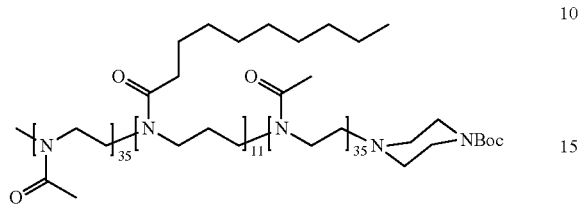

10

Me-MeOx$_{35}$-NonOzi$_{11}$-MeOx$_{35}$-PipBoc was synthesized according to GSP 1

| Initiation: | MeOTf | 0.14 g | (0.9 mmol; 1 eq) |
|---|---|---|---|
| 1. Block: | MeOx | 2.58 g | (6.18 mol; 35 eq) |
| 2. Block: | NonOzi | 2.05 g | (3.53 mol; 11 eq) |
| 3. Block: | MeOx | 2.58 g | (6.18 mol; 35 eq) |
| Termination: | PipBoc | 0.49 g | (1.77 mmol; 3 eq) |
| Solvent | PhCN | 16 mL | |
| Yield: | 6.92 g (0.8 mmol; 94%) of a white powder | | |
| M | 8.5 kg/mol | | |
| GPC (HFIP) | $M_n$ = 4.6 kg/mol; Đ = 1.22 | | |
| $^1$H-NMR | $M_n$ = 6.5 kg/mol (Me-MeOx$_{27}$-b-NonOzi$_8$-b-MeOx$_{27}$-PipBoc) (CDCl$_3$, 300.12 MHz; 298K): δ = 3.58-3.36 (br, 214H, N—CH$_2$—CH$_2$); 3.36-3.18 (br, 34H, N—CH$_2$—CH$_2$—CH$_2$); 3.07-2.94 (br, 3H, CH$_3$—N); 2.34-2.19 (br, 16H, CO—CH$_2$—(CH$_2$)$_7$—CH$_3$); 2.19-1.97 (br, 162H, CO—CH$_3$); 1.89-1.69 (br, 31H, CO—CH$_2$—CH$_2$—(CH$_2$)$_6$—CH$_3$); 1.69-1.50 (br, 42H, N—CH$_2$—CH$_2$—CH$_2$); 1.48-1.42 (br, 7H, PipBoc); 1.37-1.18 (br, 96H, CO—(CH$_2$)$_2$—(CH$_2$)$_6$—CH$_3$; 0.93-0.81 (br, 24H, CO—(CH$_2$)$_8$—CH$_3$). | | |

Me-MeOx$_{36}$-EtHepOx$_{13}$-MeOx$_{36}$-PipBoc (Reference Polymer)

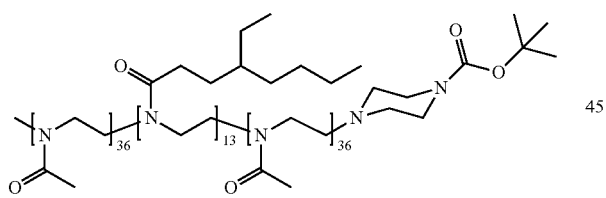

40

45

Me-MeOx$_{36}$-EtHepOx$_{13}$-MeOx$_{36}$-PipBoc was synthesized according to GSP 1

| Initiation: | MeOTf | 0.27 g | (1.63 mmol; 1 eq) |
|---|---|---|---|
| 1. Block: | MeOx | 5.0 g | (58.8 mol; 36 eq) |
| 2. Block: | EtHepOx | 4.08 g | (2.07 mol; 13 eq) |
| 3. Block: | MeOx | 5.03 g | (59.1 mol; 36 eq) |
| Termination: | PipBoc | 0.91 g | (4.89 mmol; 3 eq) |
| Solvent | PhCN | 30 mL | |
| Yield: | 12.7 g (1.43 mmol; 88%) of a white powder | | |
| M | 8.9 kg/mol | | |
| GPC (HFIP) | $M_n$ = 4.9 kg/mol; Đ = 1.16 | | |
| $^1$H-NMR | $M_n$ = 8.9 kg/mol (Me-MeOx$_{37}$-b-EtHepOx$_{12}$-b-MeOx$_{37}$-PipBoc) (CDCl$_3$, 300.12 MHz; 298K): δ = 3.80-3.14 (br, 339H, N—CH$_2$—CH$_2$); 3.07-2.92 (br, 3H, CH$_3$—N); 2.38-2.23 (br, 14H, CO—(CH$_2$)—CH$_2$—CH—) 2.23-1.99 (br, 223H, CO—CH$_3$); 2.00-1.75 (br, 11H, CO—(CH$_2$)$_2$—CH—); 1.46-1.41 (br, 9H, -PipBoc); 1.36-1.14 (br, 112H, CO—(CH$_2$)$_2$—CH—CH$_2$—CH$_3$; CO—(CH$_2$)$_2$—CH—(CH$_2$)$_3$—CH$_3$ 0.94-0.76 (br, 75H, CO—(CH$_2$)$_2$—CH—CH$_2$—CH$_3$; CO—(CH$_2$)$_2$—CH—(CH$_2$)$_3$—CH$_3$). | | |

Me-MeOx$_{36}$-EtHepOzi$_{11}$-MeOx$_{36}$-PipBoc

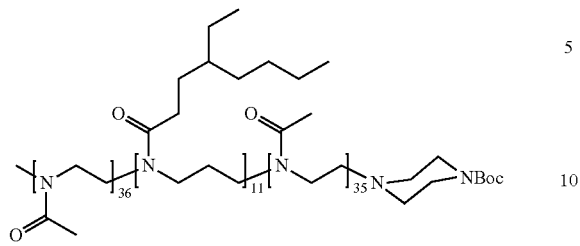

Me-MeOx$_{36}$-EtHepOzi$_{11}$-MeOx$_{36}$-PipBoc was synthesized according to GSP 1

| Initiation: | MeOTf | 0.28 g | (1.71 mmol; 1 eq) |
|---|---|---|---|
| 1. Block: | MeOx | 5.16 g | (60.7 mol; 36 eq) |
| 2. Block: | EtHepOzi | 4.02 g | (19.1 mol; 11 eq) |
| 3. Block: | MeOx | 5.17 g | (60.8 mol; 36 eq) |
| Termination: | PipBoc | 0.96 g | (5.13 mmol; 3 eq) |
| Solvent | PhCN | 30 mL | |
| Yield | 13.3 g (1.53 mmol; 89%) of a white powder | | |
| M | 9.7 kg/mol | | |
| GPC (HFIP) | $M_n$ = 4.4 kg/mol; Đ = 1.15 | | |
| $^1$H-NMR | $M_n$ = 9.5 kg/mol (Me-MeOx$_{40}$-b-EtHepOzi$_{12}$-b-MeOx$_{40}$-PipBoc) (CDCl$_3$, 300.12 MHz; 298K): δ = 3.75-3.36 (br, 322H, N—CH$_2$—CH$_2$); 3.35-3.16 (br, 49H, N—CH$_2$—CH$_2$—CH$_2$) 3.09-2.92 (br, 3H, CH$_3$—N); 2.35-2.19 (br, 22H, CO—(CH$_2$)—CH$_2$—CH—) 2.18-2.00 (br, 240H, CO—CH$_3$); 1.98-1.70 (br, 45H, CO—(CH$_2$)$_2$—CH—; N—CH$_2$—CH$_2$—CH$_2$—); 1.46-1.43 (br, 10H, -PipBoc); 1.37-1.12 (br, 106H, CO—(CH$_2$)$_2$—CH—CH$_2$—CH$_3$; CO—(CH$_2$)$_2$—CH—(CH$_2$)$_3$—CH$_3$ 0.97-0.76 (br, 72H, CO—(CH$_2$)$_2$—CH—CH$_2$—CH$_3$; CO—(CH$_2$)$_2$—CH—(CH$_2$)$_3$—CH$_3$). | | |

Me-MeOx$_{35}$-PrOzi$_{20}$-MeOx$_{35}$-PipBoc

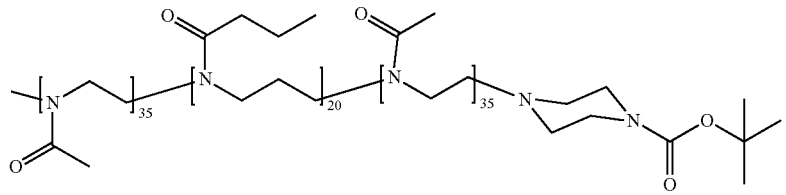

Me-MeOx$_{35}$-PrOzi$_{20}$-MeOx$_{35}$-PipBoc was synthesized according to GSP 1

| Initiation: | MeOTf | 0.96 g | (5.85 mmol; 1 eq), |
|---|---|---|---|
| 1. Block: | MeOx | 17.6 g | (0.21 mol; 35 eq) |
| 2. Block: | PrOzi | 15.0 g | (0.12 mol; 20 eq) |
| 3. Block: | MeOx | 17.6 g | (0.21 mol; 35 eq) |
| Termination: | Boc-Pip | 3.27 g | (17.6 mmol, 3 eq) |
| | K$_2$CO$_3$ | 0.81 g | (5.85 mmol; 1 eq) |
| Solvent | PhCN | 120 mL | |
| Yield: | 37.1 g (4.4 mmol; 75%) of a white powder | | |
| $M_w$ | 8.4 kg/mol | | |
| $^1$H-NMR | $M_n$ = 8.2 kg/mol (Me-MeOx$_{33}$-b-PrOzi$_{19}$-b-MeOx$_{33}$-PipBoc) (CDCl$_3$, 300.12 MHz; 298K): δ = 3.78-3.37 (br, 258H, H$^1$); 3.37-3.15 (br, 81H H$^2$); 3.09-3.02 (br, 3H, H$^3$), 2.35-2.19 (br, 39H, H$^4$); 2.19-2.00 (br, 197H, H$^5$); 1.92-1.73 (br, 37H, H$^6$), 1.73-1.51 (br, 57H, H$^7$); 1.50-1.41 (s, 9H, H$^8$); 1.05-0.83 (br, 58H, H$^9$). | | |

Me-MeOx₃₅-b-iPrOzi₁₈-b-MeOx₃₅-PipBoc

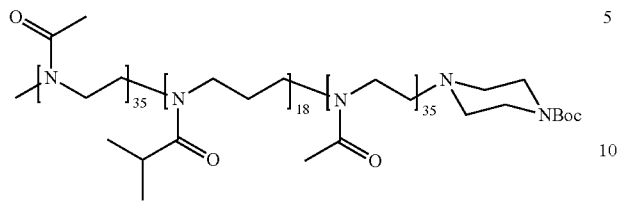

Me-MeOx₃₅-b-iPrOzi₂₀-b-MeOx₃₅-PipBoc was synthesized according to GSP 1

| | | | |
|---|---|---|---|
| Initiation: | MeOTf | 0.26 g | (1.6 mmol; 1 eq) |
| 1. Block: | MeOx | 4.7 g | (55.2 mmol; 35 eq) |
| 2. Block: | iPrOzi | 3.59 g | (28.2 mmol; 18 eq) |
| 3. Block: | MeOx | 4.77 g | (56.1 mmol; 35 eq) |
| Termination: | Boc-Pip | 0.88 g | (4.7 mmol; 3 eq) |
| Solvent | PhCN | 29 mL | |
| Yield | 8.98 g (1.06 mmol; 67%) of a white powder | | |
| M | 8.4 kg/mol | | |
| GPC (DMF) | $M_n$ = 5.9 kg/mol; Đ = 1.26 | | |
| ¹H-NMR | $M_n$ = 7.3 kg/mol (Me-MeOx₃₀-b-iPrOzi₁₆-b-MeOx₃₀-PipBoc) (CDCl₃, 300.12 MHz; 298K): δ = 3.59-3.36 (br, 243H, N—CH₂CH₂); 3.36-3.19 (br, 66H, N—CH₂—CH₂—CH₂—); 3.08-2.93 (m, 3H, N—CH₃); 2.77-2.60 (br, 15H, CO—CH—(CH₃)₂); 2.46-2.40 (br, 2H, —CH₂N—(CH₂)₂—(Pip)); 2.20-2.00 (m, 182H, CO—CH₃); 1.91-1.65 (br, 42H, N—CH₂—CH₂—CH₂—); 1.48-1.42 (m, 10H, —C—(CH₃)₃); 1.18-1.01 (m, 117H, CO—CH—(CH₃)₂) ppm. | | |

Me-MeOx₃₄-b-iPrOx₂₀-b-MeOx₃₅-PipBoc (Reference Polymer)

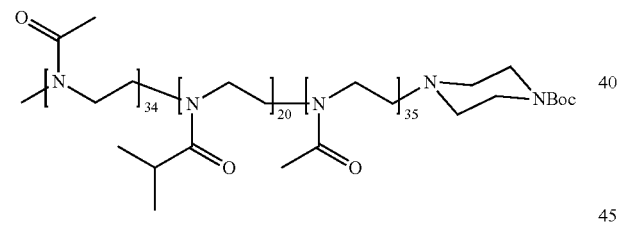

Me-MeOx₃₅-b-iPrOx₂₀-b-MeOx₃₅-PipBoc was synthesized according to GSP 1

| | | | |
|---|---|---|---|
| Initiation: | MeOTf | 0.18 g | (1.1 mmol; 1 eq) |
| 1. Block: | MeOx | 3.28 g | (38.6 mmol; 34 eq) |
| 2. Block: | iPrOx | 2.57 g | (22.8 mmol; 20 eq) |
| 3. Block: | MeOx | 3.38 g | (39.7 mmol; 35 eq) |
| Termination: | Boc-Pip | 0.68 g | (3.7 mmol; 3 eq) |
| Solvent | PhCN | 29 mL | |
| Yield | 8.46 g (1.0 mmol; 90%) of a white powder | | |
| M | 8.4 kg/mol | | |
| GPC (DMF) | $M_n$ = 6.2 kg/mol; Đ = 1.20 | | |
| ¹H-NMR | $M_n$ = 7.9 kg/mol (Me-MeOx₃₃-b-iPrOx₂₀-b-MeOx₃₃-PipBoc) (CDCl₃, 300.12 MHz; 298K): δ = 3.58-3.31 (br, 345H, N—CH₂CH₂); 3.09-3.01 (m, 3H, N—CH₃); 2.46-2.40 (br, 2H, —CH₂N—(CH₂)₂—(Pip)); 2.20-1.98 (m, 201H, CO—CH₃); 1.88-1.77 (br, 26H, CO—CH—(CH₃)₂; 1.48-1.42 (m, 9H, —C—(CH₃)₃); 1.18-1.01 (m, 117H, CO—CH—(CH₃)₂) ppm. | | |

Me-MeOx$_{36}$-b-cPrOzi$_{18}$-b-MeOx$_{36}$-PipBoc

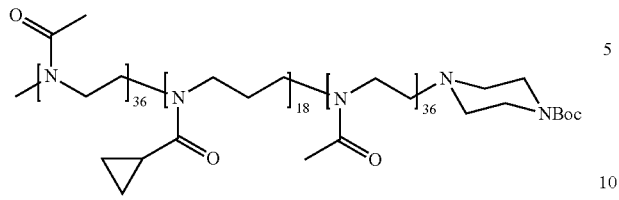

Me-MeOx$_{36}$-b-cPrOzi$_{18}$-b-MeOx$_{36}$-PipBoc was synthesized according to GSP 1

| | | | |
|---|---|---|---|
| Initiation: | MeOTf | 0.43 g | (2.61 mmol; 1 eq) |
| 1. Block: | MeOx | 7.94 g | (93.3 mmol; 36 eq) |
| 2. Block: | cPrOzi | 6.0 g | (47.9 mmol; 18 eq) |
| 3. Block: | MeOx | 7.90 g | (92.8 mmol; 36 eq) |
| Termination: | Boc-Pip | 1.46 g | (7.83 mmol; 3 eq) |
| | K$_2$CO$_3$ | 0.44 g | (2.61 mmol; 1 eq) |
| Solvent | PhCN | 50 mL | |
| Yield | 17.07 g (1.98 mmol; 67%) of a white powder | | |
| M | 8.6 kg/mol | | |
| GPC (HFIP) | M$_n$ = 4.8 kg/mol; Đ = 1.23 | | |
| $^1$H-NMR | M$_n$ = 8.1 kg/mol (Me-MeOx$_{34}$-b-cPrOzi$_{17}$-b-MeOx$_{34}$-PipBoc) (CDCl$_3$, 300.12 MHz; 298K): δ = 3.76-3.19 (br, 327H, N—CH$_2$CH$_2$, N—CH$_2$—CH$_2$—CH$_2$—); 3.07-2.90 (m, 3H, N—CH$_3$); 2.56-2.36 (br, 4H, —CH$_2$N—(CH$_2$)$_2$—(Pip)); 2.21-1.94 (m, 203H, CO—CH$_3$); 1.95-1.53 (br, 48H, N—CO—CH—(CH$_2$)$_2$, N—CH$_2$—CH$_2$—CH$_2$—); 1.48-1.39 (s, 9H, —C—(CH$_3$)$_3$); 1.04-0.60 (d, 67H, CO—CH—(CH$_2$)$_2$) ppm. | | |

Me-MeOx$_{35}$-b-cPrOx$_{18}$-b-MeOx$_{35}$-PipBoc (Reference Polymer)

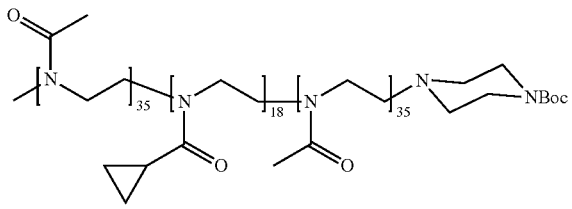

Me-MeOx$_{35}$-b-cPrOx$_{18}$-b-MeOx$_{35}$-PipBoc was synthesized according to GSP 1

| | | | |
|---|---|---|---|
| Initiation: | MeOTf | 0.12 g | (0.74 mmol; 1 eq) |
| 1. Block: | MeOx | 2.23 g | (26.2 mmol; 35 eq) |
| 2. Block: | cPrOx | 1.64 g | (13.1 mmol; 18 eq) |
| 3. Block: | MeOx | 2.25 g | (26.4 mmol; 36 eq) |
| Termination: | Boc-Pip | 0.42 g | (2.25 mmol; 3 eq) |
| | K$_2$CO$_3$ | 0.10 g | (0.75 mmol; 1 eq) |
| Solvent | PhCN | 15 mL | |
| Yield | 5.36 g (0.65 mmol; 88%) of a white powder | | |
| M | 8.2 kg/mol | | |
| GPC (HFIP) | M$_n$ = 3.3 kg/mol; Đ = 1.17 | | |
| $^1$H-NMR | M$_n$ = 8.0 kg/mol (Me-MeOx$_{34}$-b-cPrOx$_{18}$-b-MeOx$_{34}$-PipBoc) (CDCl$_3$, 300.12 MHz; 298K): δ = 3.80-3.18 (br, 351H, N—CH$_2$CH$_2$); 3.07-2.93 (m, 3H, N—CH$_3$); 2.20-1.98 (m, 206H, CO—CH$_3$); 2.0-1.73 (br, 35H, N—CO—CH—(CH)$_2$, H$_2$O); 1.49-1.39 (s, 8H, —C—(CH$_3$)$_3$); 1.02-0.70 (d, 73H, CO—CH—(CH$_2$)$_2$) ppm. | | |

Me-MeOx$_{35}$-PrOzi$_{20}$-PipBoc (Reference Polymer)

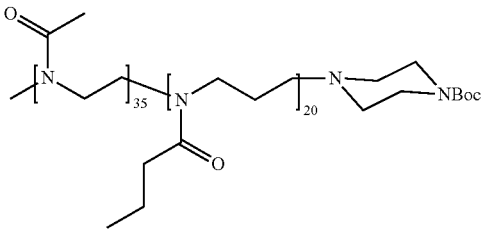

Me-MeOx$_{35}$-b-PrOzi$_{20}$-PipBoc was synthesized according to GSP 1

| | | | |
|---|---|---|---|
| Initiation: | MeOTf | 0.18 g | (1.1 mmol; 1 eq) |
| 1. Block: | MeOx | 3.14 g | (36.9 mmol; 35 eq) |
| 2. Block: | PrOzi | 2.90 g | (22.8 mmol; 20 eq) |
| Termination: | Boc-Pip | 0.70 g | (3.74 mmol; 3 eq) |
| Solvent | PhCN | 12 mL | |
| Yield | 4.91 g (0.86 mmol; 78%) of a white powder | | |
| M | 5.7 kg/mol | | |
| GPC (HFIP) | M$_n$ = 3.9 kg/mol; Đ = 1.12 | | |
| $^1$H-NMR | M$_n$ = 6.3 kg/mol (Me-MeOx$_{37}$-b-PrOzi$_{23}$-PipBoc) (CDCl$_3$, 300.12 MHz; 298K): δ = 3.72-3.38 (br, 150H, N—CH$_2$CH$_2$); | | |

-continued 3.38-3.10 (br, 89H, N—CH$_2$—CH$_2$—CH$_2$—); 3.08-2.93 (m, 3H, N—CH$_3$); 2.33-2.18 (br, 45H, CO—CH$_2$—CH$_2$—CH$_3$); 2.19-1.99 (m, 112H, CO—CH$_3$); 1.94-1.54 (br, 114H, N—CH$_2$—CH$_2$—CH$_2$—, CO—CH$_2$—CH$_2$—CH$_3$); 1.51-1.43 (s, 11H, —C—(CH$_3$)$_3$); 1.05-0.82 (m, 68H, CO—CH$_2$—CH$_2$—CH$_3$) ppm.

Me-PrOzi$_{20}$-MeOx$_{35}$-PipBoc (Reference Polymer)

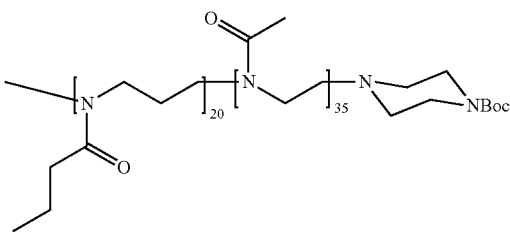

Me-PrOzi$_{20}$-b-MeOx$_{35}$-PipBoc was synthesized according to GSP 1

| | | | |
|---|---|---|---|
| Initiation: | MeOTf | 0.28 g | (1.7 mmol; 1 eq) |
| 1. Block: | PrOzi | 4.4 g | (34.9 mmol; 20 eq) |
| 2. Block: | MeOx | 5.08 g | (61.2 mmol; 35 eq) |
| Termination: | Boc-Pip | 0.96 g | (5.10 mmol; 3 eq) |
| Solvent | PhCN | 21 mL | |
| Yield | 8.01 g (1.40 mmol; 82%) of a white powder | | |
| M | 5.7 kg/mol | | |
| GPC (HFIP) | $M_n$ = 3.7 kg/mol; Đ = 1.14 | | |
| $^1$H-NMR | $M_n$ = 5.7 kg/mol (Me-PrOzi$_{20}$-MeOx$_{35}$-PipBoc) (CDCl$_3$, 300.12 MHz; 298K): δ = 3.81-3.37 (br, 143H, N—CH$_2$CH$_2$); 3.37-3.11 (br, 84H, N—CH$_2$—CH$_2$—CH$_2$—); 3.03-2.88 (m, 3H, N—CH$_3$); 2.34-2.19 (br, 41H, CO—CH$_2$—CH$_2$—CH$_3$); 2.19-1.99 (m, 106H, CO—CH$_3$); 1.96-1.54 (br, 90H, N—CH$_2$—CH$_2$—CH$_2$—, CO—CH$_2$—CH$_2$—CH$_3$); 1.51-1.40 (s, 10H, —C—(CH$_3$)$_3$); 1.04-0.84 (m, 61H, CO—CH$_2$—CH$_2$—CH$_3$) ppm. | | |

Tests

Nuclear Magnetic Resonance Spectroscopy (NMR)

NMR spectra were recorded on a Fourier 300 ($^1$H; 300.12 MHz), Bruker Biospin (Rheinstetten, Germany) at 298 K. The spectra were calibrated to the signals of residual protonated solvent signals (CDCl$_3$: 7.26 ppm; or to the internal standard sodium 3-(trimethylsilyl)tetradeuteriopropionat (TMSP) (0.00 ppm). Multiplicities of signals are depicted as follows: s, singlet; d, doublet; t, triplet; q, quartet; quin, quintet; dt; doublet of triplets; m, multiplet; b, broad.

Gel Permeation Chromatography (GPC)

Gel permeation chromatography (GPC) was performed on a Polymer Standard Service (PSS, Mainz, Germany) system (pump mod. 1260 infinity, RI-detector mod. 1260 infinity, precolumn GRAM 10 μM (50×8 mm), 30 Å PSS GRAM 10 μM (300×8 mm) and 1000 Å PSS GRAM 10 μM (300×8 mm)), with DMF (containing 1 g/L (11.5 mM) LiBr) or HFIP (containing 3 g/L potassium trifluoroacetate (KTFA)) as eluent and calibrated against PEG standards. Columns were kept at 40° C. and the flow rate was set to 1 mL/min (DMF) or 0.7 mL/min (HFIP). Prior to each measurement, samples were filtered through 0.2 μm teflon filter (Rotilabo, Karlsruhe).

Drug Solubilization

Polymer micelles loaded with the model drug curcumin (CUR) were prepared using the thin film method (R. Luxenhofer, A. Schulz, C. Rogues, S. Li, T. K. Bronich, E. V. Batrakova, R. Jordan, A. V. Kabanov, *Biomaterials* 2010, 31, 4972-4979). Ethanolic polymer (20 g/L for 10 g/L final polymer concentration; 50 g/L for 50 g/L final polymer concentration), paclitaxel (20 g/L) and curcumin (5.0 g/L) stock solutions or methanolic atorvastatin stock solutions (20 g/L) were mixed in desired ratio. After complete removal of the solvent at 50°-60° C., the films were dried in vacuo 0.2 mbar) for at least 3 hours (final polymer concentration: 10 g/L) or overnight (final polymer concentration: 50 g/L). Subsequently, preheated (37° C.) H$_2$O (Millipore) or PBS was added to obtain final polymer and drug concentrations as tested. Complete solubilization was facilitated by shaking the solutions at 1250 rpm at 55° C. for 10 min-15 min (10 g/L polymer concentration) or at least 25 min (50 g/L polymer concentration) with a Thermomixer comfort, Eppendorf AG (Hamburg, Germany). Non-solubilized drug (if any) was removed by centrifugation for 5 min at 10.000 rpm (5.000 g) with a 3-Speed micro centrifuge, neoLab (Heidelberg, Germany). Solubilization experiments were performed with 3 samples and results are presented as means±standard deviation (SD).

Curcumin quantification was performed by UV-Vis absorption on a BioTek Eon Microplate Spectrophotometer, Thermo Fisher Scientific (MA, USA) using a calibration curve obtained with known amounts of CUR. Samples were prepared in Rotilabo F-Type 96 well plates, Carl Roth GmbH & Co. KG (Karlsruhe, Germany) with a constant volume of 100 μL. Spectra were recorded from 260-600 nm at a constant reading speed of 1 nm at 298 K. Curcumin absorption was detected at 428 nm. Prior to UV-Vis absorption measurements, the aqueous formulations got diluted with ethanol to give a final absorbance between 0.3 and 2.5 (diluted at least 1:20). The following equations were used to calculate loading capacity (LC) and loading efficiency (LE):

$$LC = \frac{m_{drug}}{m_{drug} + m_{excipient}} \cdot 100\%$$

$$LE = \frac{m_{drug}}{m_{drug,added}} \cdot 100\%$$

where $m_{drug}$ and $m_{excipient}$ are the weight amounts of the solubilized drug and polymer excipient in solution and $m_{drug,added}$ is the weight amount of the drug initially added to the dispersion. No loss of polymer during micelles preparation was assumed.

HPLC analysis was carried out on a LC-20A Prominence HPLC, Shimadzu (Duisburg, Germany) equipped with a system controller CBM-20A, a solvent delivery unit LC-20 AT (double plunger), an on-line degassing unit DGU-20A, an auto-sampler SIL-20AC, a photo-diode array detector SPD-M20A, a column oven CTO-20AC, and a refractive index detector RID-20A. As stationary phase, a ZORBAX Eclipse Plus, Agilent (Santa Clara, CA, USA) C18 column (4.6×100 mm; 3.5 μm 50 mm×4 mm) was used.

Quantification of curcumin (CUR), demethoxycurcumin (DMC), bisdemethoxycurcumin (BDMC), paclitaxel (PTX)

and atorvastatin (Ator) was performed with a stepwise gradient. Within the first 10 min, the ratio of $H_2O$/ACN was decreased from 60/40 (v/v) to 40/60 (v/v). Solvent ratio was kept constant for 5 min, prior to re-increase it to initial ratio of 60/40 (v/v) within 0.5 min. This ratio was kept for 5 min. Flow rate was 1 mL/min at 40° C. Detection was performed at 220 nm (PTX and Ator) and 425 nm (CUR, DMC, BDMC). Retention times $R_t$ were 9.6 min (PTX), 11.0 min (Ator), 8.1 min (CUR), 7.3 min (DMC) and 6.5 min (BDMC). Prior to each measurement, samples were centrifuged (10.000 rpm; 5000 g) with a Speed-micro centrifuge, neoLab (Heidelberg, Germany) and filtered through 0.4 µM filter (Rotilabo, Karlsruhe, Germany). Paclitaxel and Atorvastatin quantification was performed using a calibration curve obtained with known amounts of PTX and Ator, respectively. The results are shown in the tables below and in the annexed figures.

As shown in FIGS. 1 and 2, the reference polymer Prop-MeOx$_{35}$-b-BuOx$_{20}$-b-MeOx$_{35}$-Pip exhibited loading capacities LCs up to 24.4±1.1 wt % (10 g/L polymer, FIG. 1) and 21.6±0.7 wt % (50 g/L polymer, FIG. 2) with corresponding amounts of solubilized CUR of 3.2±0.2 g/L and 13.7±0.5 g/L respectively. However, the polymers in accordance with the present invention, Prop-MeOx$_{35}$-b-BuOzi$_{20}$-b-MeOx$_{35}$-PipBoc and Prop-MeOx$_{35}$-b-PrOzi$_{20}$-b-MeOx$_{35}$-PipBoc, exhibited outstanding high drug loadings of 37.4±0.5 g/L (with 50 g/L Prop-MeOx$_{35}$-b-BuOzi$_{20}$-b-MeOx$_{35}$-PipBoc, FIG. 2) and 54.5±0.2 g/L (with 50 g/L Prop-MeOx$_{35}$-b-PrOzi$_{20}$-b-MeOx$_{35}$-PipBoc, FIG. 2).

The drug loading of Prop-MeOx$_{35}$-b-BuOx$_{20}$-b-MeOx$_{35}$-Pip increased with increasing CUR feed. However, at CUR concentrations ≥5 g/L (10 g/L P2) and ≥30 g/L (50 g/L P2), respectively, the formulations collapsed and the amount of solubilized CUR dramatically decreased to almost 0 g/L. Prop-MeOx$_{35}$-b-PrOzi$_{20}$-b-MeOx$_{35}$-PipBoc and Prop-MeOx$_{35}$-b-BuOzi$_{20}$-b-MeOx$_{35}$-PipBoc did not display this effect. As Prop-MeOx$_{35}$-b-BuOzi$_{20}$-b-MeOx$_{35}$-PipBoc reached its maximum CUR content (9.4 g/L CUR with 10 g/L polymer; 37.4 g/L CUR with 50 g/L polymer), additional CUR feed only marginally affected drug loadings, with more and more curcumin starting to precipitate.

TABLE 1

Solubilized aqueous curcumin (CUR) concentrations, loading efficiencies LE and loading capacities LC in dependence of the curcumin feed by the reference polymer Prop-MeOx$_{35}$-b-BuOx$_{20}$-b-MeOx$_{35}$-Pip.
Polymer concentration = 10 g/L.
Data is given as means ± SD (n = 3).

| curcumin feed [g/L] | solubilized curcumin [g/L] | LE [%] | LC [%] |
|---|---|---|---|
| 0.5 | 0.46 ± 0.01 | 92.1 ± 2.1 | 4.4 ± 0.1 |
| 1.0 | 0.88 ± 0.00 | 87.8 ± 0.5 | 8.1 ± 0.0 |
| 2.5 | 2.12 ± 0.10 | 84.7 ± 3.9 | 17.5 ± 0.7 |
| 3.5 | 3.23 ± 0.18 | 92.4 ± 5.4 | 24.4 ± 1.1 |
| 5.0 | 0.10 ± 0.00 | 2.0 ± 0.0 | 1.0 ± 0.0 |
| 7.5 | 0.10 ± 0.02 | 1.0 ± 0.3 | 0.7 ± 0.2 |

TABLE 2

Solubilized aqueous curcumin (CUR) concentrations, loading efficiencies LE and loading capacities LC in dependence of the curcumin feed by Prop-MeOx$_{35}$-b-BuOzi$_{20}$-b-MeOx$_{35}$-PipBoc.
Polymer concentration = 10 g/L.
Data is given as means ± SD (n = 3).

| curcumin feed [g/L] | solubilized curcumin [g/L] | LE [%] | LC [%] |
|---|---|---|---|
| 0.5 | 0.45 ± 0.02 | 89.4 ± 4.0 | 4.3 ± 0.2 |
| 1.0 | 0.89 ± 0.07 | 88.6 ± 7.4 | 8.1 ± 0.6 |
| 2.5 | 2.22 ± 0.14 | 88.8 ± 5.7 | 18.2 ± 1.0 |
| 3.5 | 2.73 ± 0.31 | 77.9 ± 8.82 | 21.4 ± 1.9 |
| 5.0 | 3.88 ± 0.54 | 77.6 ± 10.9 | 27.9 ± 2.8 |
| 7.5 | 5.52 ± 0.32 | 73.6 ± 4.3 | 35.5 ± 1.3 |
| 9.0 | 8.47 ± 0.07 | 94.2 ± 0.8 | 45.9 ± 0.2 |
| 10.5 | 9.42 ± 0.61 | 89.7 ± 5.8 | 48.5 ± 1.7 |
| 13 | 9.43 ± 0.38 | 72.5 ± 2.9 | 48.5 ± 1.0 |

TABLE 3

Solubilized aqueous curcumin (CUR) concentrations, loading efficiencies LE and loading capacities LC in dependence of the curcumin feed by Prop-MeOx$_{35}$-b-PrOzi$_{20}$-b-MeOx$_{35}$-PipBoc.
Polymer concentration = 10 g/L.
Data is given as means ± SD (n = 3).

| curcumin feed [g/L] | solubilized curcumin [g/L] | LE [%] | LC [%] |
|---|---|---|---|
| 0.5 | 0.38 ± 0.01 | 76.2 ± 1.7 | 3.7 ± 0.1 |
| 1.0 | 0.80 ± 0.03 | 80.4 ± 3.3 | 7.4 ± 0.3 |
| 2.5 | 2.28 ± 0.05 | 91.2 ± 2.0 | 18.6 ± 0.3 |
| 3.5 | 3.12 ± 0.15 | 89.2 ± 4.2 | 23.8 ± 0.8 |
| 5.0 | 4.45 ± 0.09 | 89.0 ± 1.8 | 30.8 ± 0.4 |
| 7.5 | 6.76 ± 0.05 | 90.1 ± 0.6 | 40.3 ± 0.2 |
| 9.0 | 8.52 ± 0.14 | 94.6 ± 1.5 | 46.0 ± 0.4 |
| 10.5 | 10.00 ± 0.18 | 95.2 ± 1.7 | 50.0 ± 0.4 |
| 13 | 11.91 ± 0.59 | 91.6 ± 4.5 | 54.3 ± 1.3 |

TABLE 4

Solubilized aqueous curcumin (CUR) concentrations, loading efficiencies LE and loading capacities LC in dependence of the curcumin feed by the reference polymer Prop-MeOx$_{35}$-b-BuOx$_{20}$-b-MeOx$_{35}$-Pip.
Polymer concentration = 50 g/L.
Data is given as means ± SD (n = 3).

| curcumin feed [g/L] | solubilized curcumin [g/L] | LE [%] | LC [%] |
|---|---|---|---|
| 5 | 4.76 ± 0.20 | 93.1 ± 3.3 | 8.5 ± 0.3 |
| 10 | 8.67 ± 0.49 | 86.7 ± 4.9 | 14.8 ± 0.7 |
| 15 | 13.74 ± 0.53 | 91.6 ± 3.6 | 21.6 ± 0.7 |
| 20 | 8.45 ± 0.46 | 42.2 ± 2.3 | 14.5 ± 0.7 |
| 30 | 0.08 ± 0.07 | 0.3 ± 0.2 | 0.2 ± 0.2 |

TABLE 5

Solubilized aqueous curcumin (CUR) concentrations, loading efficiencies LE and loading capacities LC in dependence of the curcumin feed by Prop-MeOx$_{35}$-b-BuOzi$_{20}$-b-MeOx$_{35}$-PipBoc. Polymer concentration = 50 g/L. Data is given as means ± SD (n = 3).

| curcumin feed [g/L] | solubilized curcumin [g/L] | LE [%] | LC [%] |
|---|---|---|---|
| 5 | 4.76 ± 0.20 | 95.3 ± 3.9 | 8.7 ± 0.3 |
| 10 | 9.00 ± 0.57 | 90.0 ± 5.7 | 15.2 ± 0.8 |
| 15 | 13.62 ± 0.41 | 90.8 ± 2.7 | 21.4 ± 0.5 |
| 20 | 16.06 ± 0.94 | 80.3 ± 4.7 | 24.3 ± 1.1 |
| 30 | 28.08 ± 0.32 | 93.6 ± 1.1 | 36.0 ± 0.3 |
| 40 | 39.74 ± 0.72 | 93.6 ± 1.3 | 42.8 ± 0.3 |
| 60 | 39.62 ± 0.62 | 79.2 ± 1.5 | 41.9 ± 0.3 |

TABLE 6

Solubilized aqueous curcumin (CUR) concentrations, loading efficiencies LE and loading capacities LC in dependence of the curcumin feed by Prop-MeOx$_{35}$-b-PrOzi$_{20}$-b-MeOx$_{35}$-PipBoc. Polymer concentration = 50 g/L. Data is given as means ± SD (n = 3).

| curcumin feed [g/L] | solubilized curcumin [g/L] | LE [%] | LC [%] |
|---|---|---|---|
| 5 | 3.91 ± 0.17 | 78.2 ± 3.1 | 7.2 ± 0.3 |
| 10 | 8.79 ± 0.28 | 87.9 ± 2.6 | 14.9 ± 0.4 |
| 15 | 12.37 ± 0.12 | 82.5 ± 0.8 | 19.8 ± 0.1 |
| 20 | 16.12 ± 0.70 | 80.6 ± 3.3 | 24.4 ± 0.8 |
| 30 | 29.95 ± 0.61 | 99.8 ± 2.0 | 37.5 ± 0.5 |
| 40 | 39.74 ± 0.72 | 99.4 ± 1.8 | 44.3 ± 0.4 |
| 60 | 54.53 ± 0.15 | 90.9 ± 0.3 | 52.2 ± 0.1 |

TABLE 7

Solubilized aqueous curcumin (CUR) concentrations, loading efficiencies LE and loading capacities LC in dependence of the curcumin feed by the reference polymer Me-MeOx$_{35}$-NonOx$_{12}$-MeOx$_{35}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 0.04 ± 0.00 | 2.2 ± 0.1 | 0.4 ± 0.0 |
| 4 | 0.45 ± 0.17 | 11.4 ± 4.2 | 4.3 ± 1.6 |
| 6 | 1.43 ± 0.13 | 23.8 ± 2.2 | 12.5 ± 1.3 |
| 8 | 3.21 ± 2.46 | 40.1 ± 30.7 | 24.3 ± 19.7 |
| 10 | 1.49 ± 0.68 | 14.9 ± 6.8 | 13.0 ± 6.4 |

TABLE 8

Solubilized aqueous curcumin (CUR) concentrations, loading efficiencies LE and loading capacities LC in dependence of the curcumin feed by Me-MeOx$_{35}$-NonOzi$_{11}$-MeOx$_{35}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 1.97 ± 0.12 | 98.3 ± 5.8 | 16.4 ± 1.1 |
| 4 | 3.89 ± 0.30 | 97.3 ± 7.4 | 28.0 ± 2.9 |
| 6 | 4.46 ± 0.28 | 74.3 ± 4.6 | 30.8 ± 2.7 |
| 8 | 5.24 ± 2.75 | 65.5 ± 34.4 | 34.4 ± 21.6 |
| 10 | 7.90 ± 0.24 | 79.0 ± 2.4 | 44.1 ± 2.4 |
| 12 | 5.30 ± 3.61 | 44.2 ± 30.1 | 34.7 ± 26.5 |
| 14 | 1.68 ± 0.29 | 12.0 ± 2.0 | 14.4 ± 2.8 |

TABLE 9

Solubilized aqueous curcumin (CUR) concentrations, loading efficiencies LE and loading capacities LC in dependence of the curcumin feed by the reference polymer Me-MeOx$_{36}$-EtHepOx$_{13}$-MeOx$_{36}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 0.00 ± 0.00 | 0.2 ± −0.1 | 0.0 ± 0.0 |
| 4 | 1.88 ± 0.14 | 47.1 ± 3.5 | 15.9 ± 1.4 |
| 6 | 2.79 ± 1.08 | 46.6 ± 17.9 | 21.8 ± 9.7 |
| 8 | 2.39 ± 0.45 | 29.8 ± 5.7 | 19.3 ± 4.3 |
| 10 | 3.33 ± 0.30 | 33.3 ± 3.0 | 25.0 ± 2.9 |

TABLE 10

Solubilized aqueous curcumin (CUR) concentrations, loading efficiencies LE and loading capacities LC in dependence of the curcumin feed by Me-MeOx$_{36}$-EtHepOzi$_{11}$-MeOx$_{36}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 2.15 ± 0.12 | 107.6 ± 6.1 | 17.7 ± 1.2 |
| 4 | 3.06 ± 0.21 | 76.5 ± 5.2 | 23.4 ± 2.0 |
| 6 | 3.81 ± 0.40 | 63.4 ± 6.7 | 27.6 ± 3.9 |
| 8 | 5.74 ± 0.44 | 71.8 ± 5.5 | 36.5 ± 4.2 |
| 10 | 4.39 ± 1.80 | 43.9 ± 18.0 | 30.5 ± 15.3 |

TABLE 11

Solubilized aqueous atorvastatin (Ator) concentrations, loading efficiencies LE and loading capacities LC in dependence of the atorvastatin feed by the reference polymer Prop-MeOx$_{35}$-b-BuOx$_{20}$-b-MeOx$_{35}$-Pip. Polymer concentration = 10 g/L. Data is given as means ± SD (n = 3).

| atorvastatin feed [g/L] | atorvastatin solublized [g/L] | LE [%] | LC [%] |
|---|---|---|---|
| 5 | 2.21 ± 1.13 | 44.2 ± 22.6 | 18.1 ± 10.1 |
| 8 | 2.65 ± 0.81 | 33.1 ± 10.1 | 20.9 ± 7.5 |

TABLE 12

Solubilized aqueous atorvastatin (Ator) concentrations, loading efficiencies LE and loading capacities LC in dependence of the atorvastatin feed by Prop-MeOx$_{35}$-b-BuOzi$_{20}$-b-MeOx$_{35}$-PipBoc. Polymer concentration = 10 g/L. Data is given as means ± SD (n = 3).

| atorvastatin feed [g/L] | atorvastatin solubilized [g/L] | LE [%] | LC [%] |
|---|---|---|---|
| 5 | 3.92 ± 0.45 | 78.4 ± 8.9 | 28.2 ± 4.3 |
| 8 | 5.84 ± 0.79 | 73.0 ± 9.9 | 36.9 ± 7.3 |

TABLE 13

Achieved co-formulated aqueous curcumin (CUR) and paclitaxel (PTX) concentrations, loading efficiencies LE and loading capacities LC in dependence of the drug feed concentrations. Polymer concentration Me-MeOx$_{35}$-PrOzi$_{20}$-MeOx$_{35}$-PipBoc = 10 g/L. Data isgiven as means ± SD (n = 3).

| drug | drug feed [g/L] | solubilized drug [g/L] | loading efficiency [%] | loading capacity [%] |
|---|---|---|---|---|
| Curcumin | 2 | 2.20 ± 0.16 | 110.1 ± 8.2 | 18.0 ± 1.6 |
| Paclitaxel | 2 | 1.68 ± 0.03 | 84.0 ± 0.0 | 14.4 ± 0.3 |
| CUR & PTX | 4 | 3.88 | 97.0 | 28.0 |
| Curcumin | 4 | 4.24 ± 0.24 | 106.0 ± 6.0 | 29.8 ± 2.3 |
| Paclitaxel | 4 | 3.28 ± 0.04 | 82.0 ± 0.0 | 24.7 ± 0.4 |
| CUR & PTX | 8 | 7.52 | 94.0 | 42.9 |
| Curcumin | 6 | 5.07 ± 0.31 | 84.6 ± 5.2 | 33.7 ± 3.0 |
| Paclitaxel | 6 | 4.75 ± 0.00 | 79.1 ± 0.0 | 32.2 ± 0.3 |
| CUR & PTX | 12 | 9.82 | 81.8 | 49.5 |
| Curcumin | 8 | 7.68 ± 0.84 | 96.0 ± 10.6 | 43.4 ± 7.8 |
| Paclitaxel | 8 | 6.05 ± 0.10 | 75.7 ± 0.0 | 37.7 ± 1.0 |
| CUR & PTX | 16 | 13.73 | 85.8 | 57.9 |
| Curcumin | 10 | 7.12 ± 0.71 | 71.24 ± 7.1 | 41.6 ± 6.6 |
| Paclitaxel | 10 | 7.04 ± 0.37 | 70.4 ± 0.0 | 41.3 ± 3.5 |
| CUR & PTX | 20 | 14.16 | 70.8 | 58.6 |

TABLE 14

Solubilized aqueous curcumin (CUR) concentrations, loading efficiencies LE and loading capacities LC in dependence of the curcumin feed by the polymer Me-MeOx$_{35}$-b-cPrOx$_{18}$-b-MeOx$_{35}$-PipBoc (reference polymer). Polymer concentration = 10 g/L. Data is given as means ± SD (n = 3).

| curcumin feed [g/L] | solubilized curcumin [g/L] | LE [%] | LC [%] |
|---|---|---|---|
| 2 | 1.04 ± 0.04 | 52.1 ± 1.9 | 9.4 ± 0.4 |
| 4 | 0.08 ± 0.06 | 2.0 ± 1.5 | 0.8 ± 0.6 |
| 6 | 0.55 ± 0.03 | 9.1 ± 0.5 | 5.2 ± 0.3 |
| 8 | 0.18 ± 0.02 | 2.3 ± 0.2 | 1.8 ± 0.2 |
| 10 | 0.05 ± 0.01 | 0.5 ± 0.1 | 0.5 ± 0.1 |
| 12 | 0.01 ± 0.00 | 0.1 ± 0.0 | 0.1 ± 0.0 |

TABLE 15

Solubilized aqueous curcumin (CUR) concentrations, loading efficiencies LE and loading capacities LC in dependence of the curcumin feed by the polymer Me-MeOx$_{36}$-b-cPrOzi$_{18}$-b-MeOx$_{36}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 1.96 ± 0.04 | 97.9 ± 2.1 | 16.4 ± 0.4 |
| 4 | 3.65 ± 0.07 | 91.3 ± 1.7 | 26.7 ± 0.7 |
| 6 | 5.22 ± 0.21 | 86.9 ± 3.4 | 34.3 ± 2.0 |
| 8 | 7.14 ± 0.16 | 89.2 ± 2.0 | 41.7 ± 1.6 |
| 10 | 8.00 ± 0.05 | 80.0 ± 0.5 | 44.4 ± 0.5 |
| 12 | 11.60 ± 0.26 | 96.7 ± 2.1 | 53.7 ± 2.5 |

TABLE 16

Solubilized aqueous curcumin (CUR) concentrations, loading efficiencies LE and loading capacities LC in dependence of the curcumin feed by the polymer Me-MeOx$_{35}$-b-iPrOx$_{20}$-b-MeOx$_{35}$-PipBoc (reference polymer). Polymer concentration = 10 g/L. Data is given as means ± SD (n = 3).

| curcumin feed [g/L] | solubilized curcumin [g/L] | LE [%] | LC [%] |
|---|---|---|---|
| 2 | 1.59 ± 0.09 | 79.7 ± 4.7 | 13.7 ± 0.9 |
| 4 | 1.50 ± 0.04 | 37.4 ± 1.0 | 13.0 ± 0.4 |
| 6 | 0.81 ± 0.09 | 13.4 ± 1.6 | 7.5 ± 0.9 |
| 8 | 0.73 ± 0.02 | 9.1 ± 0.2 | 6.8 ± 0.2 |
| 10 | 0.49 ± 0.01 | 4.9 ± 0.1 | 4.6 ± 0.1 |
| 12 | 0.66 ± 0.12 | 5.5 ± 1.0 | 6.2 ± 1.1 |

TABLE 17

Solubilized aqueous curcumin (CUR) concentrations, loading efficiencies LE and loading capacities LC in dependence of the curcumin feed by the polymer Me-MeOx$_{35}$-b-iPrOzi$_{20}$-b-MeOx$_{35}$-PipBoc. Polymer concentration = 10 g/L. Data is given as means ± SD (n = 3).

| curcumin feed [g/L] | solubilized curcumin [g/L] | LE [%] | LC [%] |
|---|---|---|---|
| 2 | 1.80 ± 0.06 | 89.9 ± 3.1 | 15.2 ± 0.6 |
| 4 | 3.49 ± 0.04 | 87.3 ± 1.1 | 25.9 ± 0.4 |
| 6 | 5.25 ± 0.20 | 87.5 ± 3.4 | 34.4 ± 2.0 |
| 8 | 6.70 ± 0.17 | 83.7 ± 2.1 | 40.1 ± 1.7 |
| 10 | 8.80 ± 0.78 | 88.0 ± 7.8 | 46.8 ± 7.3 |
| 12 | 6.84 ± 1.02 | 57.0 ± 8.5 | 40.6 ± 9.3 |

TABLE 18

Solubilized aqueous paclitaxel (PTX) concentrations, loading efficiencies LE and loading capacities LC in dependence of the Paclitaxel feed by the polymer Me-MeOx$_{35}$-b-cPrOx$_{18}$-b-MeOx$_{35}$-PipBoc (reference polymer). Polymer concentration = 10 g/L. Data is given as means ± SD (n = 3).

| paclitaxel feed [g/L] | solubilized paclitaxel [g/L] | LE [%] | LC [%] |
|---|---|---|---|
| 2 | 0.05 ± 0.00 | 2.6 ± 0.1 | 0.5 ± 0.0 |
| 4 | 0.09 ± 0.02 | 2.3 ± 0.5 | 0.9 ± 0.2 |
| 6 | 0.10 ± 0.02 | 1.7 ± 0.3 | 1.0 ± 0.2 |
| 8 | 0.06 ± 0.01 | 0.7 ± 0.1 | 0.6 ± 0.1 |
| 10 | 0.07 ± 0.04 | 0.7 ± 0.4 | 0.7 ± 0.4 |
| 12 | 0.05 ± 0.00 | 0.4 ± 0.0 | 0.5 ± 0.0 |

TABLE 19

Solubilized aqueous paclitaxel (PTX) concentrations, loading efficiencies LE and loading capacities LC in dependence of the paclitaxel feed by the polymer Me-MeOx$_{36}$-b-cPrOzi$_{18}$-b-MeOx$_{36}$-PipBoc. Polymer concentration = 10 g/L. Data is given as means ± SD (n = 3).

| paclitaxel feed [g/L] | solubilized paclitaxel [g/L] | LE [%] | LC [%] |
|---|---|---|---|
| 2  | 1.83 ± 0.07 | 91.3 ± 3.3 | 15.4 ± 0.7 |
| 4  | 2.99 ± 0.07 | 74.8 ± 1.7 | 23.0 ± 0.7 |
| 6  | 1.95 ± 0.19 | 32.5 ± 3.2 | 16.3 ± 1.9 |
| 8  | 0.58 ± 0.11 | 7.2 ± 1.4  | 5.5 ± 1.1 |
| 10 | 0.57 ± 0.33 | 5.7 ± 3.3  | 5.4 ± 3.2 |
| 12 | 0.55 ± 0.19 | 4.6 ± 1.6  | 5.2 ± 1.9 |

TABLE 20

Solubilized aqueous paclitaxel (PTX) concentrations, loading efficiencies LE and loading capacities LC in dependence of the paclitaxel feed by the polymer Me-MeOx$_{35}$-b-iPrOx$_{20}$-b-MeOx$_{35}$-PipBoc (reference polymer). Polymer concentration = 10 g/L. Data is given as means ± SD (n = 3).

| paclitaxel feed [g/L] | solubilized paclitaxel [g/L] | LE [%] | LC [%] |
|---|---|---|---|
| 2  | 1.02 ± 0.09 | 50.9 ± 4.5 | 9.2 ± 0.9 |
| 4  | 0.47 ± 0.10 | 11.7 ± 2.6 | 4.5 ± 1.0 |
| 6  | 0.13 ± 0.06 | 2.2 ± 1.1  | 1.3 ± 0.6 |
| 8  | 0.10 ± 0.02 | 1.2 ± 0.3  | 0.9 ± 0.2 |
| 10 | 0.09 ± 0.04 | 0.9 ± 0.4  | 0.9 ± 0.4 |
| 12 | 0.08 ± 0.04 | 0.6 ± 0.3  | 0.8 ± 0.4 |

TABLE 21

Solubilized aqueous paclitaxel (PTX) concentrations, loading efficiencies LE and loading capacities LC in dependence of the paclitaxel feed by the polymer Me-MeOx$_{35}$-b-iPrOzi$_{20}$-b-MeOx$_{35}$-PipBoc. Polymer concentration = 10 g/L. Data is given as means ± SD (n = 3).

| paclitaxel feed [g/L] | solubilized paclitaxel [g/L] | LE [%] | LC [%] |
|---|---|---|---|
| 2  | 1.60 ± 0.07 | 80.0 ± 3.5 | 13.8 ± 0.7 |
| 4  | 1.73 ± 0.21 | 43.2 ± 5.2 | 14.7 ± 2.1 |
| 6  | 0.55 ± 0.16 | 9.1 ± 2.7  | 5.2 ± 1.6 |
| 8  | 0.29 ± 0.26 | 3.7 ± 3.2  | 2.9 ± 2.5 |
| 10 | 0.06 ± 0.01 | 0.6 ± 0.1  | 0.6 ± 0.1 |
| 12 | 0.09 ± 0.03 | 0.8 ± 0.2  | 0.9 ± 0.3 |

TABLE 22

Solubilized aqueous curcumin (CUR) concentrations, loading efficiencies LE and loading capacities LC in dependence of the curcumin feed by the polymer Me-MeOx$_{35}$-b-cPrOzi$_{18}$-PipBoc (reference polymer). Polymer concentration = 10 g/L. Data is given as means ± SD (n = 3).

| curcumin feed [g/L] | solubilized curcumin [g/L] | LE [%] | LC [%] |
|---|---|---|---|
| 2  | 1.85 ± 0.03 | 92.4 ± 1.7 | 15.6 ± 0.3 |
| 4  | 3.56 ± 0.17 | 88.9 ± 4.2 | 26.2 ± 1.7 |
| 6  | 0.11 ± 0.04 | 1.9 ± 0.6  | 1.1 ± 0.4 |
| 8  | 0.03 ± 0.00 | 0.4 ± 0.0  | 0.3 ± 0.0 |
| 10 | 0.03 ± 0.01 | 0.3 ± 0.1  | 0.3 ± 0.1 |
| 12 | 0.04 ± 0.01 | 0.3 ± 0.1  | 0.4 ± 0.1 |

TABLE 23

Solubilized aqueous curcumin (CUR) concentrations, loading efficiencies LE and loading capacities LC in dependence of the curcumin feed by the polymer Me-PrOzi$_{18}$-b-MeOx$_{35}$-PipBoc (reference polymer). Polymer concentration = 10 g/L. Data is given as means ± SD (n = 3).

| curcumin feed [g/L] | solubilized curcumin [g/L] | LE [%] | LC [%] |
|---|---|---|---|
| 2  | 1.84 ± 0.13 | 91.8 ± 6.6 | 15.5 ± 1.3 |
| 4  | 3.40 ± 0.04 | 84.9 ± 1.1 | 25.4 ± 0.4 |
| 6  | 0.49 ± 0.15 | 8.2 ± 2.5  | 4.7 ± 1.4 |
| 8  | 0.06 ± 0.01 | 0.8 ± 0.1  | 0.6 ± 0.1 |
| 10 | 0.05 ± 0.01 | 0.5 ± 0.1  | 0.5 ± 0.1 |
| 12 | 0.03 ± 0.01 | 0.3 ± 0.1  | 0.3 ± 0.1 |

DISCUSSION OF FIGURES

FIG. 1 shows solubilized aqueous curcumin (CUR) concentrations (bars, left axis) and the corresponding loading capacities (lines, right axis) in dependence of the CUR feed by Prop-MeOx$_{35}$-b-BuOx$_{20}$-b-MeOx$_{35}$-Pip (reference polymer, empty bars, dashed line), Prop-MeOx$_{35}$-b-BuOzi$_{20}$-b-MeOx$_{35}$-PipBoc (striped bars, dotted line) and Prop-MeOx$_{35}$-b-PrOzi$_{20}$-b-MeOx$_{35}$-PipBoc (black bars, solid line). Polymer concentration=10 g/L. Data is given as means±SD (n=3).

FIG. 2 shows solubilized aqueous curcumin (CUR) concentrations (bars, left axis) and the corresponding loading capacities (lines, right axis) in dependence of the CUR feed by Prop-MeOx$_{35}$-b-BuOx$_{20}$-b-MeOx$_{35}$-Pip (reference polymer, empty bars, dashed line), Prop-MeOx$_{35}$-b-BuOzi$_{20}$-b-MeOx$_{35}$-PipBoc (striped bars, dotted line) and Prop-MeOx$_{35}$-b-PrOzi$_{20}$-b-MeOx$_{35}$-PipBoc (black bars, solid line). Polymer concentration=50 g/L. Data is given as means±SD (n=3).

FIG. 3 shows solubilized aqueous curcumin (CUR) concentrations (bars, left axis) and the corresponding loading capacities (lines, right axis) in dependence of the CUR feed by Me-MeOx$_{35}$-NonOx$_{12}$-MeOx$_{35}$-PipBoc (empty bars, dashed line), Me-MeOx$_{35}$-NonOzi$_{12}$-MeOx$_{35}$PipBoc (black bars, solid line). Polymer concentration=10 g/L. Data is given as means±SD (n=3).

FIG. 4 shows solubilized aqueous curcumin (CUR) concentrations (bars, left axis) and the corresponding loading capacities (lines, right axis) in dependence of the CUR feed by Me-MeOx$_{35}$-EtHepOx$_{12}$-MeOx$_{35}$-PipBoc (empty bars, dashed line), Me-MeOx$_{35}$-EtHepOzi$_{12}$-MeOx$_{35}$PipBoc (black bars, solid line). Polymer concentration=10 g/L. Data is given as means±SD (n=3).

FIG. 5 shows solubilized aqueous atorvastatin (Ator) concentrations (bars, left axis) and the corresponding loading capacities (lines, right axis) in dependence of the atorvastatin feed by Prop-MeOx$_{35}$-b-BuOx$_{20}$-b-MeOx$_{35}$-Pip (reference polymer, empty bars, dashed line) and Prop-MeOx$_{35}$-b-BuOzi$_{20}$-b-MeOx$_{35}$-PipBoc (striped bars, dotted line) Polymer concentration=50 g/L. Data is given as means±SD (n=3).

Figure 1:
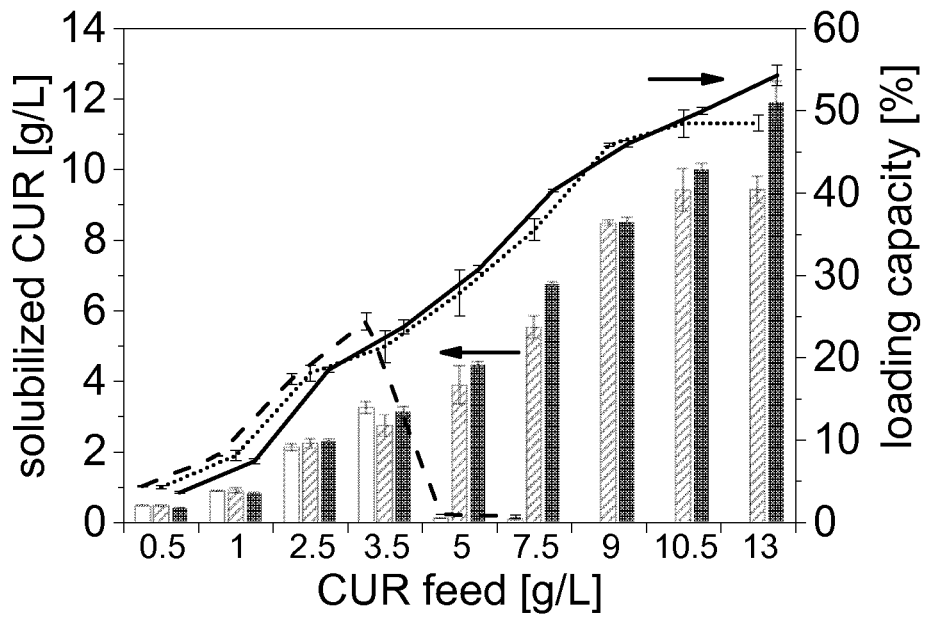
Figure 2:
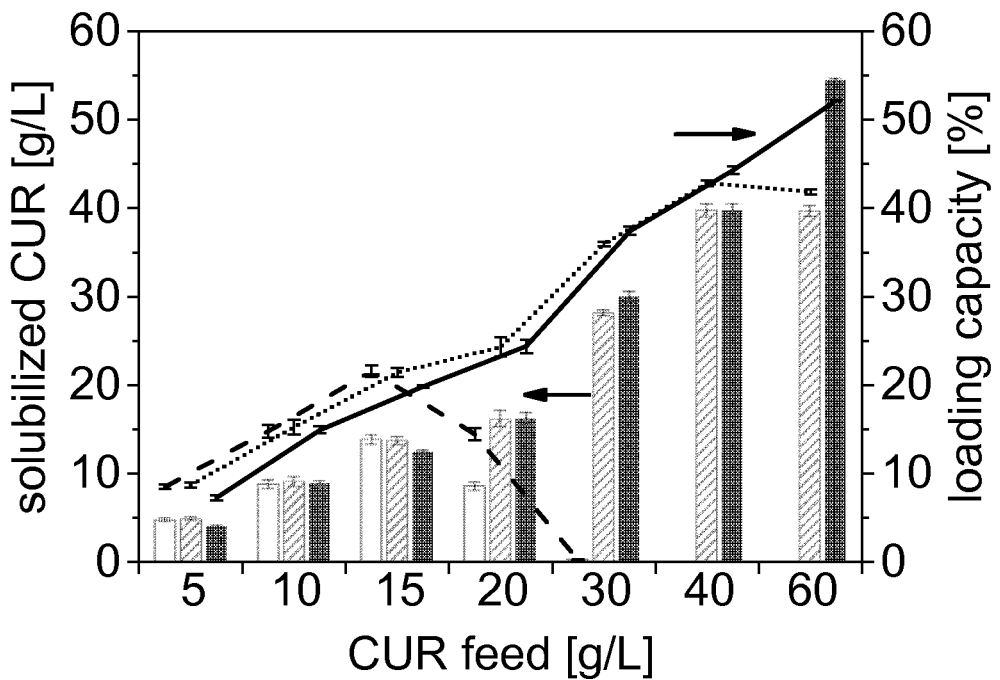
Figure 3:
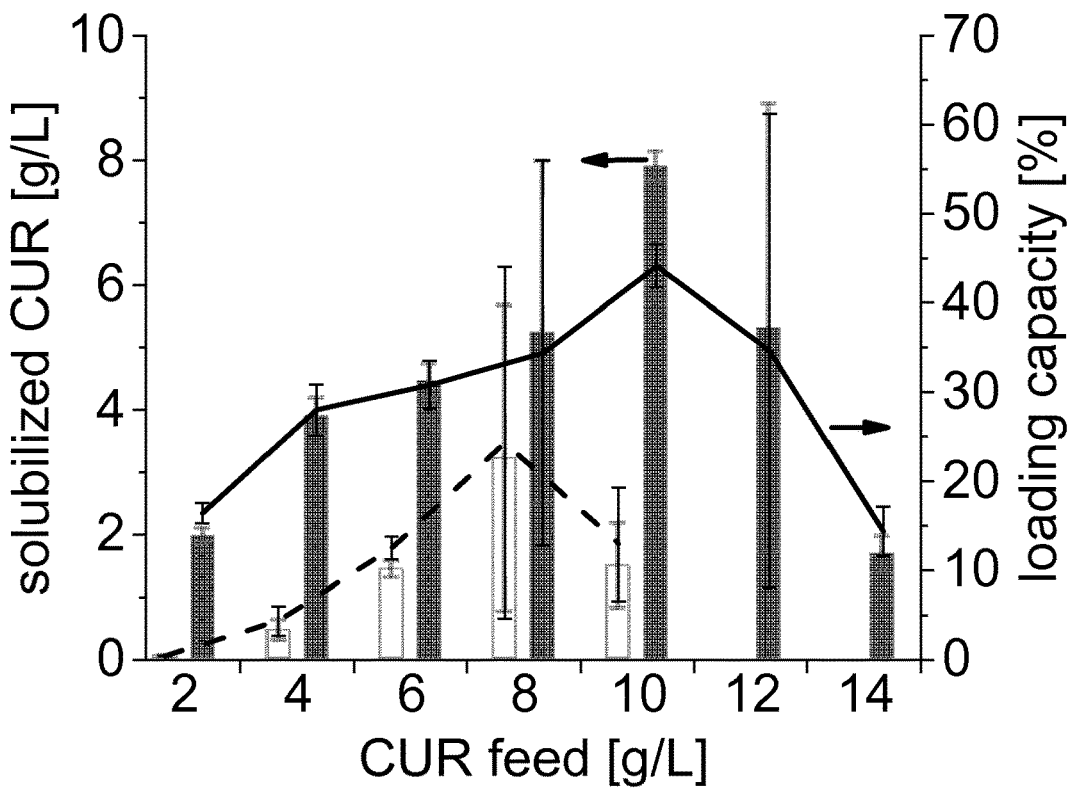
Figure 4:
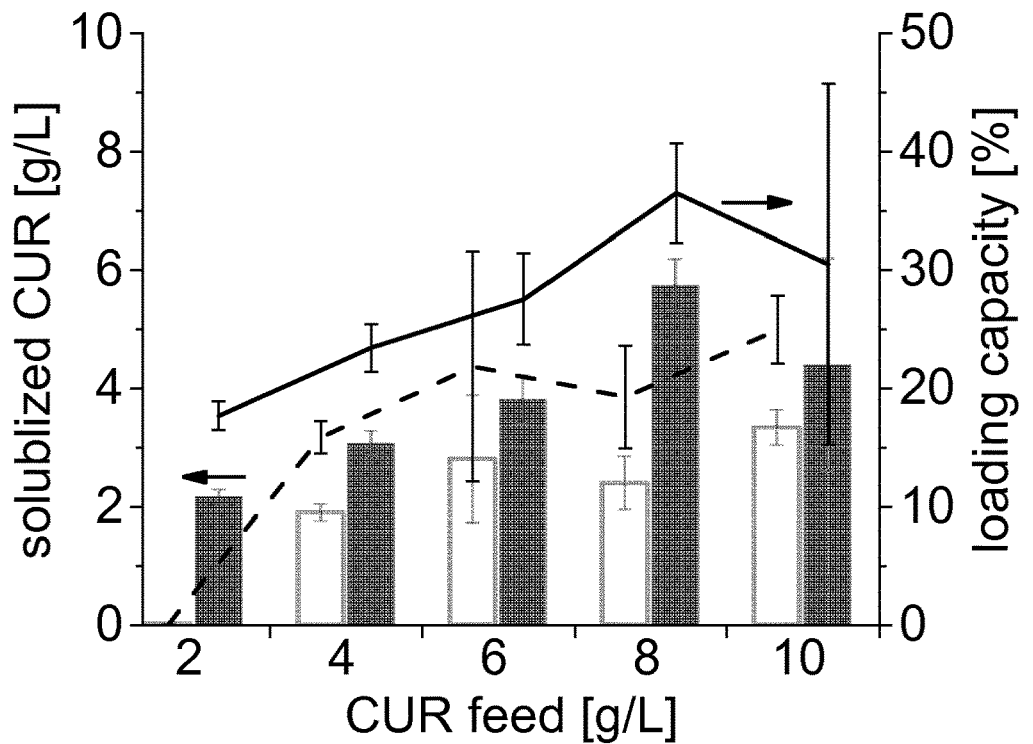
Figure 5:
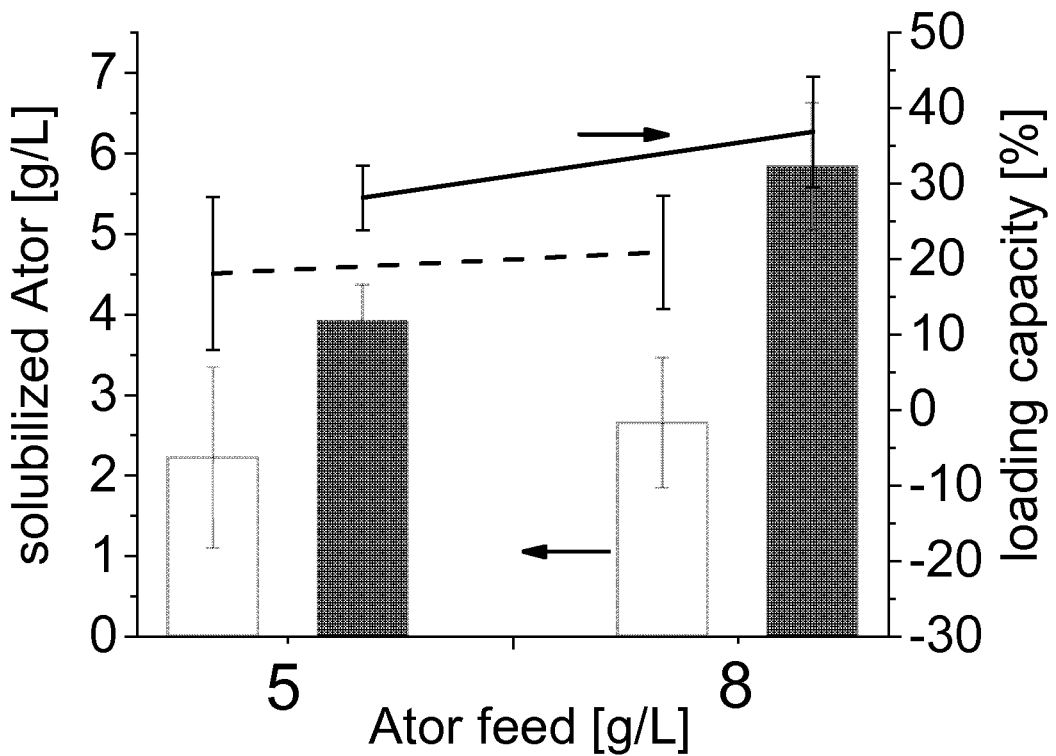
Figure 6:
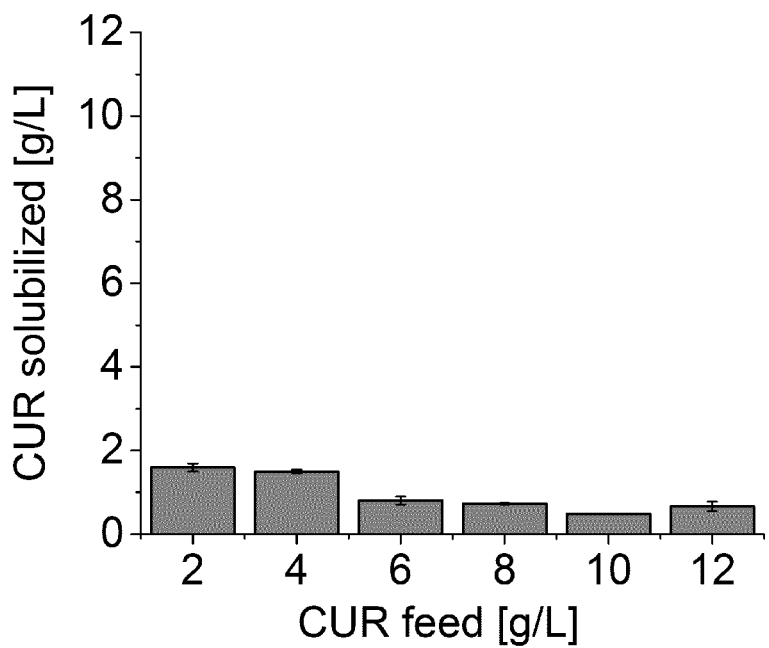
FIG. 6 shows solubilized aqueous curcumin (CUR) concentrations in dependence of the CUR feed by Me-MeOx$_{35}$-b-iPrOx$_{20}$-b-MeOx$_{35}$-PipBoc Polymer (reference polymer) concentration=10 g/L. Data is given as means±SD (n=3).
Figure 7:
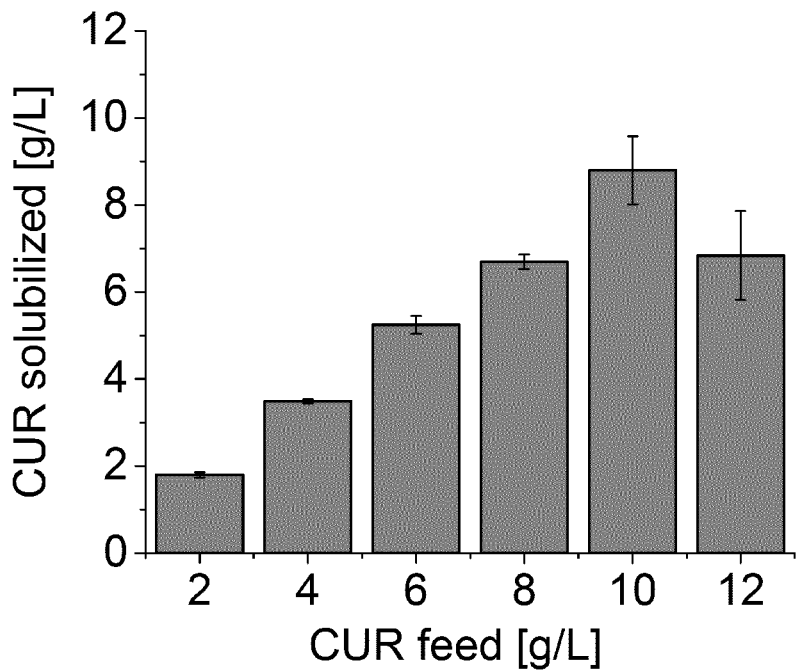
FIG. 7 shows solubilized aqueous curcumin (CUR) concentrations in dependence of the CUR feed by Me-MeOx$_{35}$-b-iPrOzi$_{20}$-b-MeOx$_{35}$-PipBoc Polymer concentration=10 g/L. Data is given as means±SD (n=3).
Figure 8:
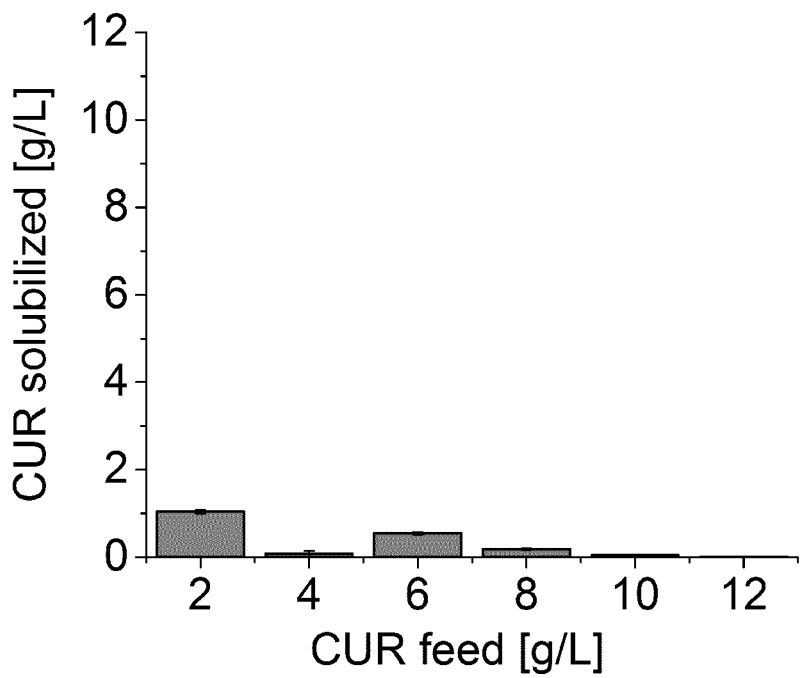
FIG. 8 shows solubilized aqueous curcumin (CUR) concentrations in dependence of the CUR feed by Me-MeOx$_{35}$-b-cPrOx$_{18}$-b-MeOx$_{35}$-PipBoc Polymer (reference polymer) concentration=10 g/L. Data is given as means±SD (n=3).
Figure 9:
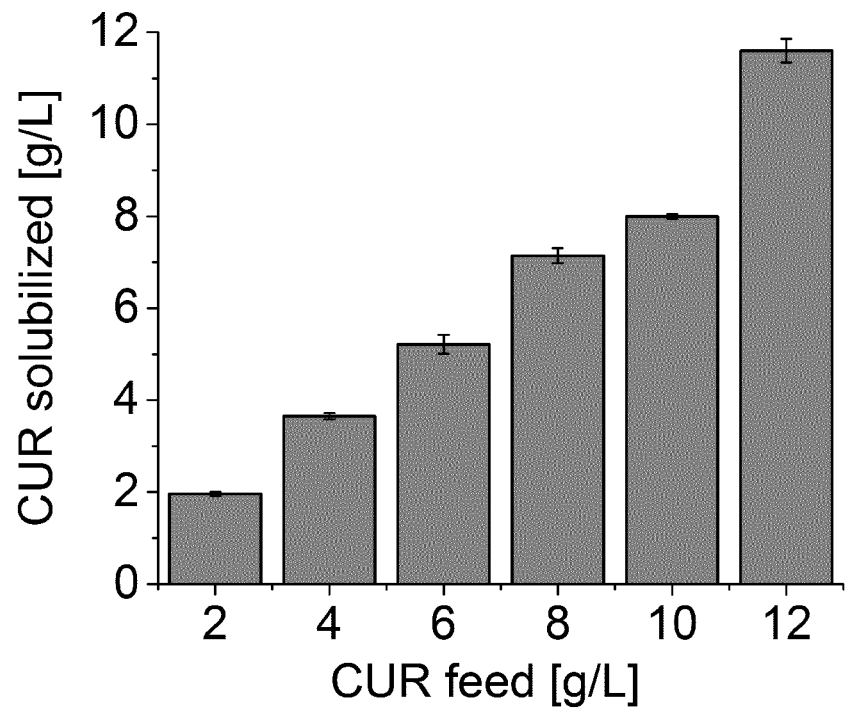
FIG. 9 shows solubilized aqueous curcumin (CUR) concentrations in dependence of the CUR feed by Me-MeOx$_{36}$-b-cPrOzi$_{10}$-b-MeOx$_{36}$-PipBoc Polymer concentration=10 g/L. Data is given as means±SD (n=3).
Figure 10:
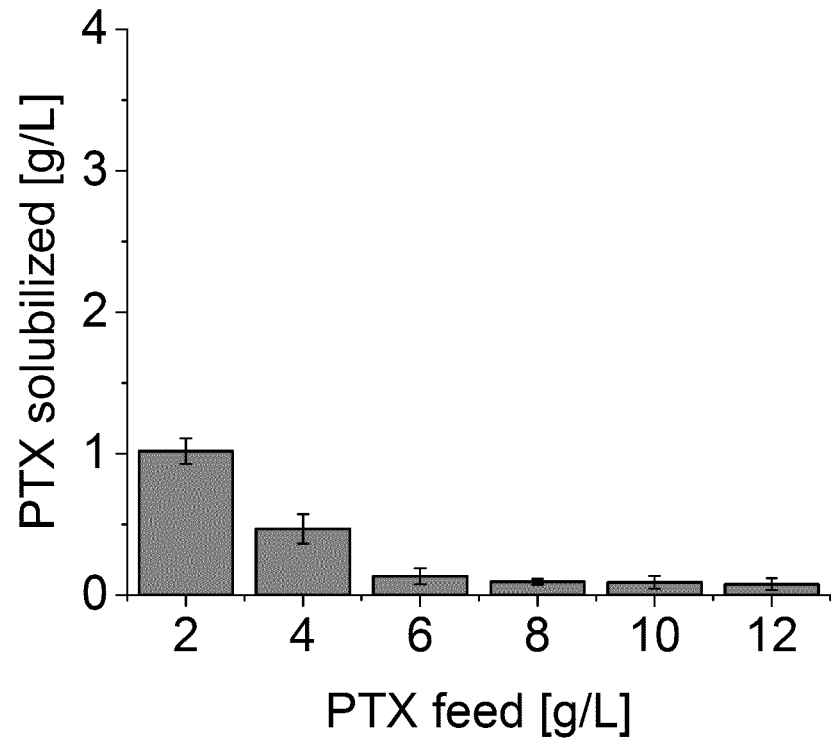
FIG. 10 shows solubilized aqueous paclitaxel (PTX) concentrations in dependence of the PTX feed by Me-MeOx$_{35}$-b-iPrOx$_{20}$-b-MeOx$_{35}$-PipBoc Polymer (reference polymer) concentration=10 g/L. Data is given as means±SD (n=3).
Figure 11:
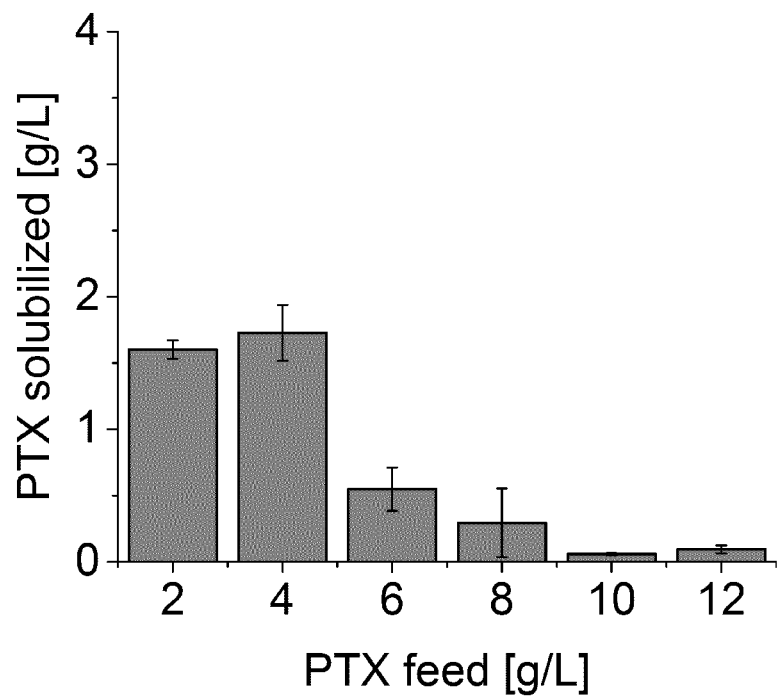
FIG. 11 shows solubilized aqueous paclitaxel (PTX) concentrations in dependence of the PTX feed by Me-MeOx$_{35}$-b-iPrOzi$_{20}$-b-MeOx$_{35}$-PipBoc Polymer concentration=10 g/L. Data is given as means±SD (n=3).
Figure 12:
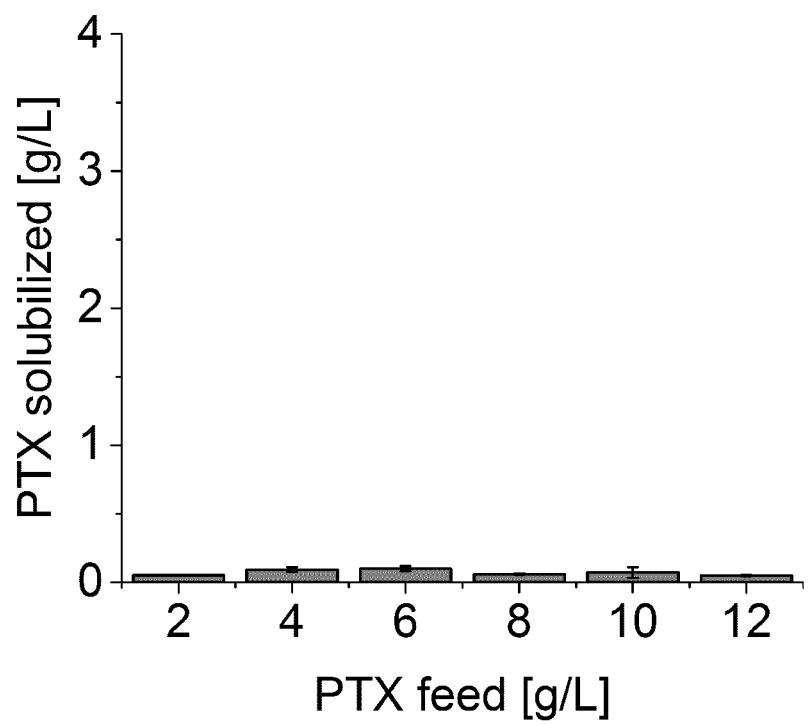
FIG. 12 shows solubilized aqueous paclitaxel (PTX) concentrations in dependence of the PTX feed by Me-MeOx$_{35}$-b-cPrOx$_{10}$-b-MeOx$_{35}$-PipBoc Polymer (reference polymer) concentration=10 g/L. Data is given as means±SD (n=3).
Figure 13:
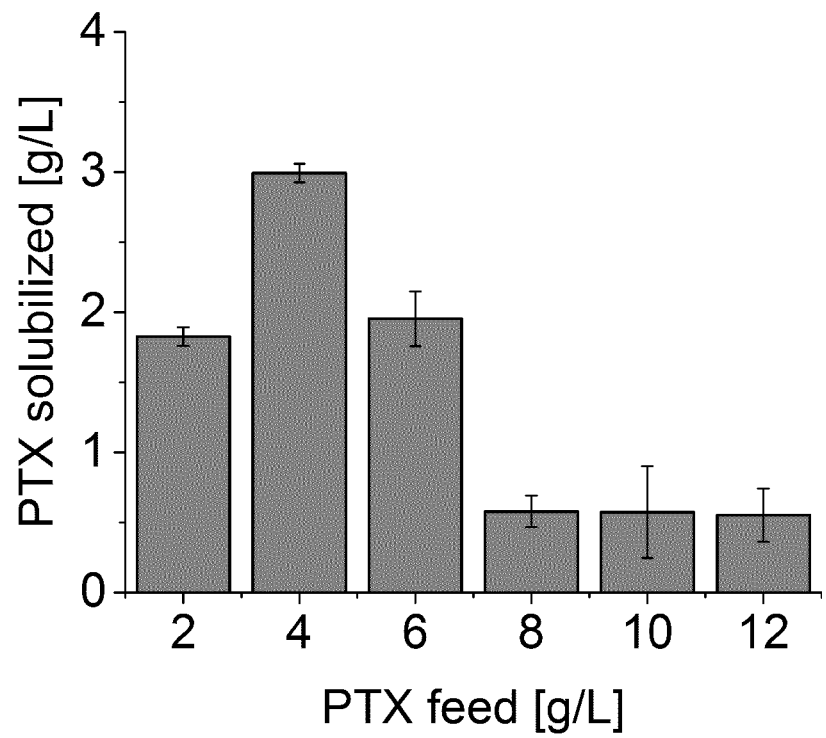
FIG. 13 shows solubilized aqueous paclitaxel (PTX) concentrations in dependence of the PTX feed by Me-MeOx$_{36}$-b-cPrOzi$_{10}$-b-MeOx$_{36}$-PipBoc Polymer concentration=10 g/L. Data is given as means±SD (n=3).
Figure 14:
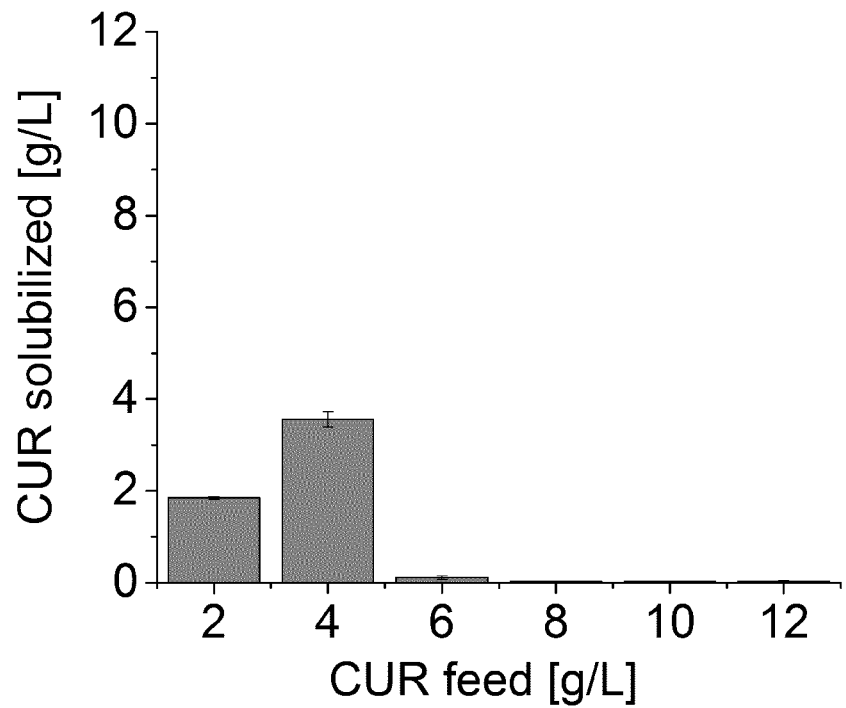

FIG. 14 shows solubilized aqueous curcumin (CUR) concentrations in dependence of the CUR feed by Me-MeOx$_{35}$-b-PrOzi$_{20}$-PipBoc (reference polymer). Polymer concentration=10 g/L. Data is given as means±SD (n=3).

Figure 15:
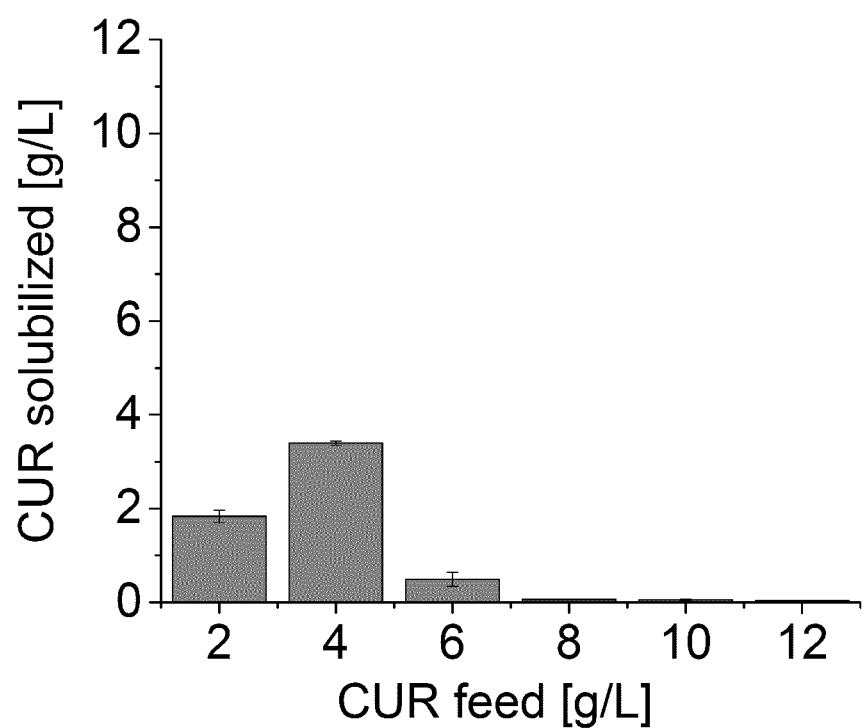

FIG. 15 shows solubilized aqueous curcumin (CUR) concentrations in dependence of the CUR feed by Me-PrOzi$_{20}$-b-MeOx$_{35}$-PipBoc (reference polymer). Polymer concentration=10 g/L. Data is given as means±SD (n=3).

The invention claimed is:

1. An (A)-(B)-(A) triblock copolymer comprising
two hydrophilic polymer blocks (A), wherein a structure of the polymer blocks (A) is indicated independently for each of the two polymer blocks, by the following formula (IIa)

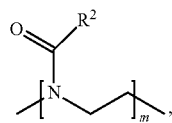

(IIa)

wherein $R^2$ is methyl or ethyl; and
m is from 20 to 50;
and
a polymer block (B), wherein a structure of the polymer block (B) is indicated by the following formula (Ia)

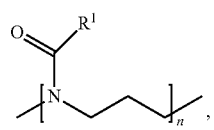

(Ia)

wherein $R^1$ is a C3-C9 alkyl group and n is from 10 to 50;
wherein the ratio of repeating units contained in polymer blocks (A) to repeating units contained in polymer block (B), in terms of the numbers of repeating units, ranges from 7:1 to 2:1.

2. The (A)-(B)-(A) triblock copolymer of claim 1, wherein $R^2$ is methyl.

3. The (A)-(B)-(A) triblock copolymer of claim 1, wherein $R^1$ is a C3-C5 alkyl group.

4. The (A)-(B)-(A) triblock copolymer of claim 1, wherein $R^1$ is selected from propyl and butyl.

5. The (A)-(B)-(A) triblock copolymer of claim 1, wherein n is 15 or more.

6. The (A)-(B)-(A) triblock copolymer of claim 1, wherein the ratio of repeating units contained in polymer blocks (A) to repeating units contained in polymer block (B), in terms of the numbers of repeating units, ranges from 7:1 to 3:1.

7. A composition comprising one or more triblock copolymers as defined in claim 1 in combination with one or more compounds to be solubilized.

8. The composition of claim 7, wherein a weight ratio of the weight of the compound(s) to be solubilized to the weight of the triblock copolymer(s) is at least 0.1:1.0.

9. The composition of claim 7, which is a solid composition.

10. The composition of claim 7, which is a solution, an emulsion or a suspension.

11. The composition of claim 10, wherein the composition comprises micelles which are formed by the triblock copolymer(s) and which incorporate the compound(s) to be solubilized.

12. The composition of claim 7, wherein the one or more triblock copolymers form micelles which incorporate the compound(s) to be solubilized.

13. The composition of claim 7, wherein the one or more compounds to be solubilized are selected from therapeutically active agents, agents for use in diagnosis, fungicides, pesticides, insecticides, herbicides, phytohormones and catalytically active compounds.

14. The composition of claim 7, which is a pharmaceutical composition which comprises one or more therapeutically active agents as the compound(s) to be solubilized.

15. The composition of claim 14, wherein the therapeutically active agent comprises a chemotherapeutic agent which is suitable for the treatment of cancer.

16. A method for treatment of cancer, comprising administrating a therapeutically effective amount of the composition of claim 15 to a patient in need thereof.

17. A method for the preparation of a pharmaceutical composition, said method comprising a step of combining a triblock copolymer of claim 1 with one or more therapeutically active agent as compounds to be solubilized.

18. A method for solubilizing one or more compounds in an aqueous environment, comprising a step of incorporating the compound(s) as compounds to be solubilized into a composition of claim 7.

19. A method for detection of one or more compounds which interact with a target of interest in a screening test, said method comprising steps of providing one or more compounds to be subjected to a detection method, separately incorporating the compound(s) as compounds to be solubilized each into a composition as defined in claim 7, and subjecting the compositions to the screening test.

* * * * *